(12) United States Patent
Durrant et al.

(10) Patent No.: US 8,273,349 B2
(45) Date of Patent: *Sep. 25, 2012

(54) BINDING MEMBER WHICH BINDS TO BOTH LEWIS-Y AND LEWIS-B HAPTENS, AND ITS USE FOR TREATING CANCER

(75) Inventors: Linda Durrant, Nottingham (GB); Tina Parsons, Nottingham (GB)

(73) Assignee: Cephalon Australia Pty Ltd, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/974,938

(22) Filed: Dec. 21, 2010

(65) Prior Publication Data

US 2011/0150906 A1 Jun. 23, 2011

Related U.S. Application Data

(63) Continuation-in-part of application No. 12/505,313, filed on Jul. 17, 2009, now Pat. No. 7,879,983, which is a continuation of application No. 11/831,125, filed on Jul. 31, 2007, now abandoned, which is a continuation of application No. 10/476,233, filed as application No. PCT/GB02/02182 on May 10, 2002, now Pat. No. 7,267,821.

(30) Foreign Application Priority Data

May 11, 2001 (GB) .................................. 0111628.4

(51) Int. Cl.
*A61K 39/395* (2006.01)

(52) U.S. Cl. ............... 424/130.1; 424/143.1; 424/144.1; 424/152.1; 424/155.1; 424/156.1

(58) Field of Classification Search .................. None
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,544,545 A | 10/1985 | Ryan et al. | |
| 4,816,397 A | 3/1989 | Boss et al. | |
| 4,816,567 A | 3/1989 | Cabilly et al. | |
| 5,225,539 A | 7/1993 | Winter | |
| 5,670,331 A * | 9/1997 | el Kouni et al. | 435/15 |
| 5,869,045 A | 2/1999 | Hellstrom et al. | |
| 7,267,821 B2 * | 9/2007 | Durrant et al. | 424/130.1 |
| 7,879,983 B2 * | 2/2011 | Durrant et al. | 530/388.1 |

FOREIGN PATENT DOCUMENTS

| | | |
|---|---|---|
| EP | 0036676 | 9/1981 |
| EP | 0052522 | 5/1982 |
| EP | 0058481 | 8/1982 |
| EP | 0088046 | 9/1983 |
| EP | 0120694 | 10/1984 |
| EP | 0125023 | 11/1984 |
| EP | 0143949 | 6/1985 |
| EP | 0184187 | 6/1986 |
| EP | 0142541 | 7/1987 |
| EP | 0239400 | 8/1994 |
| EP | 0285059 | 11/1994 |
| GB | 2188638 | 10/1987 |
| JP | 06000093 | 1/1994 |
| WO | 9311161 | 6/1993 |
| WO | 9413804 | 6/1994 |

OTHER PUBLICATIONS

Spinelli et al. JOP, Sep. 10, 2006;7(5):486-91.*
Durrant et al., "Development of Second Generation Monoclonal Antibodies Recognizing Lewis y/b Antigen by Anti-Idiotypic Immunization," Hybridoma, 12(6):647-660 (1993).
Eppstein et al., "Biological activity of liposome-encapsulated murine interferon y is mediated by a cell membrane receptor." Proc. Natl. Acad. Sci. USA, 82:3688-3692 (1985).
Abe et al., "Differential Expression of Difucosyl Type 2 Chain (LeY) Defined by Monoclonal Antibody AH6 in Different Locations of Colonic Epithelia, Various Histological Types of Colonic Polyps, and Adenocarcinomas1," Cancer Research, 42:2639-2644 (1986).
Atschul et al., "Basic Local Alignment Search Tool" J. Mol. Biol. 215:403-410 (1990).
Atschul et al., "Gapped BLAST and PSI-BLAST: a new generation of protein database search programs" Nucleic Acid Research, 25(17):3389-3402 (1997).
Bird et al., "Single-Chain Antigen-Binding Proteins" Science, 242:423-426 (1988).
Brown et al., "Immunohistochemical Localization of Y Hapten and the Structurally Related H Type-2 Blood-Group Antigen on Large-Bowel Tumours and Normal Adult Tissues," Int. J. Cancer, 33:727-736 (1984).
Brown et al., "A monoclonal antibody against human colonic adenoma recognizes difucosylated Type-2-blood-group chains," Bioscience Reports, 3:163-170 (1983).
Durrant et al., "Flow Cytometric Screening of Monoclonal Antibodies for Drug or Toxin Targeting to Human Cancer," Journal of the National Cancer Institute, 81(9):688-696 (1989).

(Continued)

Primary Examiner — Maher Haddad
(74) Attorney, Agent, or Firm — Karl Bozicevic; Bozicevic, Field & Francis LLP

(57) ABSTRACT

The invention relates to the use of a binding member which binds to Lewis$^Y$ and Lewis$^b$ haptens in the treatment of tumours and leukaemia. The binding member may be an antibody which binds to Lewis$^Y$ and Lewis$^b$ haptens and cancer cells and induces cells death.

15 Claims, 13 Drawing Sheets

OTHER PUBLICATIONS

Figure 1:
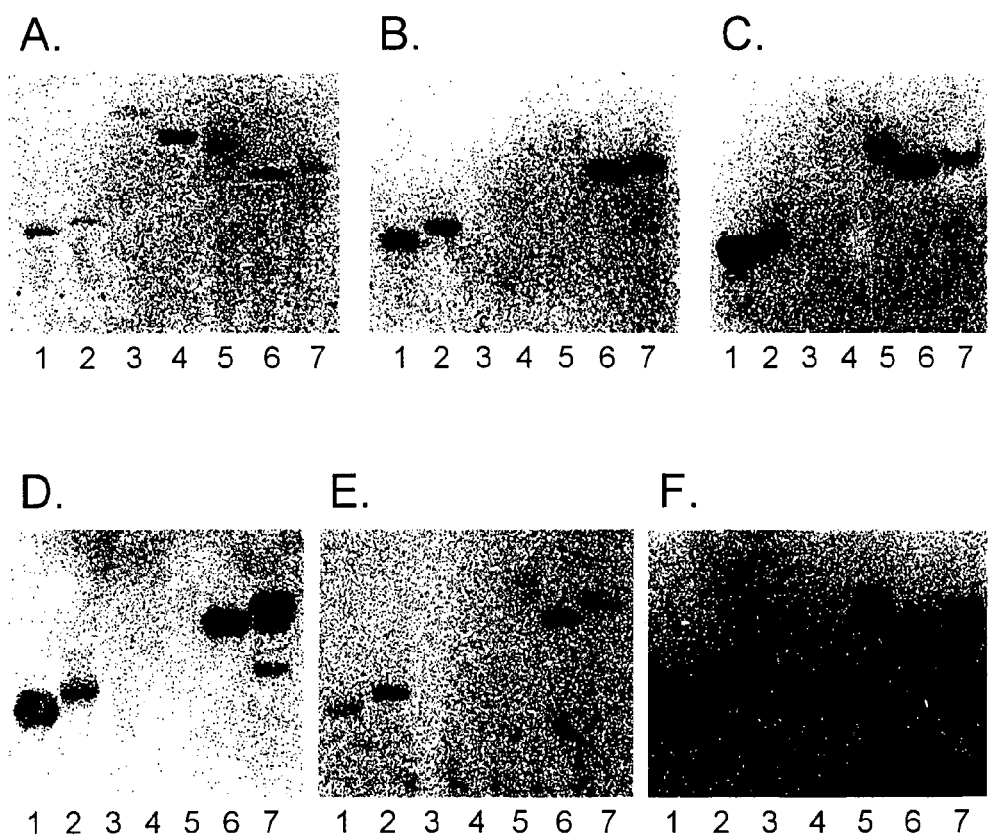

Holliger et al., "Diabodies: small bivalent and bispecific antibody fragments." Proc. Natl. Acad. Sci. USA, 90:6444-6448 (1993).

Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883 (1988).

Hwang et al., "Hepatic uptake and degradation of unilamellar sphingomyelin/cholesterol liposomes: A kinetic study," Proc. Natl. Acad. Sci. USA, 77(7):4030-4034 (1980).

Iwata et al., "High Frequency of Apoptosis in Infantile Capillary Haemangioma" Journal of Pathology, 179:403-408 (1996).

Karlin et al., "Application and statistics for multiple high-scoring segments in molecular sequences," Proc. Natl. Acad. Sci. USA, 90:5873-5877 (1993).

Karlin et al., "Methods for assessing the statistical significance of molecular sequence features by using general scoring schemes," Proc. Natl. Acad. Sci. USA, 87:2264-2268 (1990).

Kim et al., "Expression of LeY and Extended LeY Blood Group-related Antigens in Human Malignant, Premalignant and Nonmalignant Colonic Tissues," Cancer Research, 46:5985-5992 (1986).

Langer et al., "Controlled release of macromolecules," Chemtech, 12:98-105 (1982).

Langer et al., "Biocompatibility of polymeric delivery systems for macromolecules," Journal of Biomedical Materials Research, 15:267-277 (1981).

Pearson et al., "Improved tools for biological sequence comparison," Proc. Natl. Acad. Sci. USA, 85:2444-2448 (1988).

Pluckthun, A., "ANtibody Engineering: Advances from the Use of *Escherichia coli* Expressions Systems," Bio/Technology, 9:545-551 (1991).

Reff, M.E., "High-level production of recombinant immunoglobulins in mammalian cells," Current Opinion in Biology, 4:573-576 (1993).

Sidman et al., "Controlled Release of Macromolecules and Pharmaceuticals from Synthetic Polypeptides Based on Glutamic Acid," Biopolymers, 22:547-556 (1983).

Terada et al., "Detection of Apoptosis and Expression of Apoptosis-Related Proteins during Human Intrahepatic Bile Duct Development," American Journal of Pathology, 146(1):67-74 (1995).

Terada et al., "Expression of apoptosis, proliferating cell nuclear antigen, and apoptosis-related antigens(bcl-2, C-myc, Fas, Lewis(Y) and p53) in human cholangiocarcinomas and hepatocellular carcinoma," Pathol. Int., 46:764-770 (1996).

Torelli et al., "ADVANCE and ADAM: two algorithm for the analysis of global similarity between homologous informational sequences," Comput. Appl. Biosci., 10(1):3-5 (1994).

Trill et al., "Production of monoclonal antibodies in COS and CHO cells," Current Opinion in Biotechnology, 6:553-560 (1995).

Ward et al., "Binding activities of a repertoire of single immunoglobulin variable domains secreted from *Escherichia coli*," Nature, 341-544-546 (1989).

Yamada et al., "Induction of LeY Antigen by 5-Aza-2'-deoxycytidine in Association with Differentiation and Apoptosis in Human Pancreatic Cancer Cells," Anticancer Research, 16:735-740 (1996).

Madjd et al., "High expression of Lewis y/b antigens is associated with decreased survival in lymph node negative breast carcinomas," Breast Cancer Research, 7:R780-787 (2005).

Rudikoff et al., "Single amino acid substitution altering antigen-binding specificity" PNAS, 79:1979-1983 (1982).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue" J. Cell Biol., 111:2129-2138 (1990).

Lazar et al., "Leucine 48 Results in Different Biological Activities" Mol. Cell. Biol. 8:1247-1252 (1988).

Wen et al., "PTEN controls tumor-induced angiogenesis" PNAS, 98:4622-4627 (2001).

Bowie et al., "Deciphering the Message in Protein Sequences: Tolerance to Amino Acid Substitutions" Science, 257:1306-1310 (1990).

White et al., "Antibody-Targeted Immunotherapy for Treatment of Malignancy" Ann. Ref. Med., 52:125-145 (2001).

Stedman's Medical Dictionary, 25th Ed., pp. 1652-1653 (1990).

Co et al., "Humanized Anti-Lewis Y Antibodies: In Vitro Properties and Pharmacokinetics in Rhesus Monkeys" Cancer Research, 56:1118-1125 (1996).

Kong et al., "Fucosylated Glycosphingolipids of Human Myeloid Cells" Archives Biochem. Biophysics., 300 (2):677-683 (1993).

Sabbatini et al., "Immunization of Ovarian Cancer Patient's with a Synthetic Lewis Y-Protein Conjugate Vaccine: A Phase 1 Trial" Intl. J. Cancer 87(1):79-85 (2000).

Pai-Scherf et al., "Imaging and Phase I Study of 111In- and 90-Y-Labeled Anti-Lewis Y Monoclonal Antibody B3" Clin. Cancer Res., 6(5):1720-30 (2000).

Nagai et al., "Lewis Y antigen expression in normal and neoplastic cutaneous tissues" Eur. J. Dermatology, 5 (2):153-155 (1995).

Mellman, I, The Scientist, 20(1):47-56 (2006).

Bodey et al., Anticancer Res., 20:2665-2676 (2000).

Roger, I et al., Bioscience Reports, 84(4):359-368 (1988).

Durrant et al., Hybridoma, 12(6):647-660 (1993).

Baselga et al., "Recombinant Humanized Anti-HER2 Antibody (HerceptinTM) Enhances the Antitumor Activity of Paclitaxel and Doxorubicin against HER2/neu Overexpressing Human Breast Cancer Xenografts" Cancer Research, 58(13):2825-2831 (1998).

Brodin et al., "A Monoclonal Antibody that Recognizes both Leb and Y(ley) Antigens" Glycoconjugate Journal, 4 (4):399-406 (1987).

Clarke et al., "Therapeutic Efficacy of Anti-Lewisy Humanized 3S193 Radioimmunotherapy in a Breast Cancer Model: Enhanced Activity When Combined with Taxol Chemotherapy" Clinical Cancer Research, 6:3621-3628 (2000).

Emery et al., "A new monoclonal antibody (3D3) generated with human respiratory mucins and directed against Lewis determinants" Glycobiology, 5(6):563-570 (1995).

Miyake et al., "Correlation of Expression of H/Ley/Leb Antigens With Survival in Patients With Carcinoma of the Lung" New England Journal of Medicine, 327(1):14-28 (1992).

Nakamura et al., "The usefulness of anti-fucosylated antigen antibody YB-2 for diagnosis of hepatocellular carcinoma" Glycoconjugate Journal, 14L81-87 (1997).

Scott et al., "Construction, Production, and Characterization of Humanized Anti-Lewis Y Monoclonal Antibody 3S193 for Targeted Immunotherapy of Solid Tumors" Cancer Research, 60:3254-3261 (2000).

* cited by examiner

BINDING MEMBER WHICH BINDS TO BOTH LEWIS-Y AND LEWIS-B HAPTENS, AND ITS USE FOR TREATING CANCER

This application is a continuation application of Ser. No. 12/505,313, filed Jul. 17, 2009 (now U.S. Pat. No. 7,879,983), which application is a continuation application of Ser. No. 11/831,125, filed Jul. 31, 2007 (now abandoned), which application is a continuation application of Ser. No. 10/476,233, filed May 14, 2004 (now U.S. Pat. No. 7,267,821, issued Sep. 11, 2007), which application is a 371 National Phase of PCT/GB02/02182, filed May 10, 2002, which application claims priority to GB 0111628.4, filed May 11, 2001, all of which are incorporated herein by reference in their entirety noting that the current application controls to the extent there is any contradiction with an earlier application and to which applications we claim priority under 35 USC §119 and §120.

The present invention relates to the use of binding members which bind to both Lewis$^Y$ and Lewis$^b$ haptens in the treatment of tumours and leukaemia.

The Lewis antigens, which include Lewis y, b, x and a antigens, are blood group antigens. The Lewis$^Y$ hapten is a difucosylated tetrasaccharide (Fuc 1-2Galβ 1-4 (Fucα1-3) GlcNAc found on type 2 blood group oligosaccharides. This antigen is a positional isomer of the Lewis$^b$ hapten (Fuc1-2Galβ1-3 (Fucα1-4) GlNAc and a fucosylated derivative of the Lewis$^x$ hapten. The Lewis$^y$ hapten is a cell surface antigen epitope which is expressed by colorectal tumours (Abe et al., Cancer Research, 46, 2639 (1986); Kim et al., Cancer Research, 46, 5985 (1986)).

The mouse monoclonal antibody C14 was raised to the C14gp200 antigen. The mouse monoclonal antibody C14 recognises Lewis$^Y$ hapten (Brown et al, Biosci. Rep. 3, 163 (1983); Brown et al., Int. J. Cancer, 33, 727) and binds to 78% of colorectal cancers (Durrant et al., J. Natl. Cancer Inst., 81, 688 (1989)).

Other antibodies which bind to the Lewis$^Y$ hapten are known. For example, EP-B-0285059 discloses an antibody, BR-55, which reacts with both Lewis$^Y$ and B-7-2. B-7-2 has also been shown to be associated with tumour cells (EP-B-0285059). EP-B-0285059 states that the advantage of recognising two cancer-associated epitopes is that it increases the chances of recognising more tumour cells relative to normal cells. However, BR-55 relies on effector cells in order to be able to kill cells.

In addition, U.S. Pat. No. 5,869,045 discloses an antibody, BR-96, which binds to both Lewis$^Y$ and Lewis$^x$ haptens. Although U.S. Pat. No. 5,869,045 teaches that antibodies which kill cells by themselves are rare, BR-96, has been shown to have the ability to kill cancer cells in unmodified form (U.S. Pat. No. 5,869,045). Since no other Lewis$^Y$ antibody has been reported to cause direct cytotoxicity, the activity of BR-96 can be assumed to be related to it's recognition of the Lewis$^x$ hapten.

Antibodies which bind to both Lewis$^Y$ and Lewis$^b$ antigens are known. Studies have demonstrated that C14 monoclonal antibody recognises and binds to both Lewis$^Y$ and Lewis$^b$ (extended and non-extended forms) antigens (Durrant at al., Hybridoma, 12, 647-660 (1996)). A C14 monoclonal antibody specific for both Lewis$^Y$ and Lewis$^b$ antigens was raised against primary colorectal tumour cells using standard fusion protocols. The C14 antibody recognised a range of solid tumours but as it was an IgM, it was not very useful in reproducibly screening large numbers of serum samples. One of the immunological characteristics of carbohydrate antigens is that they usually elicit a T cell independent response, resulting in the production of an IgM antibody.

Subsequently, an anti-idiotyoic approach in mice was used to produce an IgG variant of the C14 (IgM) monoclonal antibody. Rats were immunised with C14 monoclonal antibody and rat anti-C14 monoclonal antibody was purified. Immunisation of mice with the rat anti-C14 antiserum and the C14gp200 antigen and subsequent fusion of the immune splenocytes with a mouse myeloma produced five IgG (two IgG3s and three IgG1s) monoclonal antibodies recognising the Lewis$^Y$ and Lewis$^b$ antigens (Durrant at al., Hybridoma, 12, 647-660 (1996)). Each of the five IgGs (referred to as the "692" monoclonal antibodies) demonstrated the same specificity as C14 (Durrant at al., Hybridoma, 12, 647-660 (1996)). These antibodies were shown by thin layer chromatography and ELISA to bind to extended and non-extended Lewis$^Y$ and Lewis$^b$ haptens but not to Lewis$^x$ or H blood group hapten. The antibodies bound to breast, lung, colorectal, gastric, and ovarian tumours and myeloid leukaemia. Recognition of normal tissue was minimal and restricted to weak staining of the upper gastrointestinal tract basement membrane, mucin staining of stomach and fallopian tubes and weak staining of liver capillaries.

The present inventors have now, surprisingly, found that antibodies which bind to both Lewis$^Y$ and Lewis$^b$ haptens induce cell death.

According to a first aspect, the present invention provides the use of a naked binding member which binds to both Lewis' and Lewis$^b$ haptens in the preparation of an agent for treating cancer.

The present invention also provides a pharmaceutical composition for the treatment of cancer, the composition which comprises a naked binding member that binds to both Lewis$^Y$ and Lewis$^b$ haptens.

The present invention further provides a method of treatment of a patient such as a mammal, such as a method of treatment of cancer in a patient (preferably human) which comprises administering to said patient an effective amount of a naked binding member which binds to both Lewis$^y$ and Lewis b haptens.

As used herein, a "binding member" is a member of a pair of molecules which have binding specificity for one another. The binding member is, therefore, a specific binding member. The members of a binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of binding pairs are antigen-antibody, biotin-avidin, hormone-hormone receptor, receptor-ligand, enzyme-substrate. The present invention is concerned with antigen-antibody type reactions, although a binding member of the invention may be any moiety which can bind to both Lewis$^Y$ and Lewis$^b$ haptens.

An "antibody" is an immunoglobulin, whether natural or partly or wholly synthetically produced. The term also covers any polypeptide, protein or peptide having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

As used herein, "naked" means that the binding member of the present invention is not bound to, or associated with, any agent having anti-tumour properties.

The term "hapten" includes epitopes and antigens. Haptens may be attached to a large carrier molecule such as a cell e.g. a tumour cell.

The binding member of the first aspect of the invention may be an antibody such as a monoclonal or polyclonal antibody, or a fragment thereof. The constant region of the antibody may be of any class including, but not limited to, human classes IgG, IgA, IgM, IgD and IgE. The antibody may belong to any sub class e.g. IgG1, IgG2, IgG3 and IgG4. IgG1 is preferred. The antibody may be SC101 (corresponds to, and used interchangeably with, "692" as described in Durrant et al., Hybridoma, 12, 647-660 1996) for example, SC101/23, SC101/29, SC101/33, SC101/42, SC101/43 or C14.

A cell line expressing an antibody which binds to both Lewis$^y$ and Lewis$^b$ haptens, specifically the cell line SC101/29 has been deposited with ECACC of CAMR, Salisbury Wilshire, SP4 0JG, United Kingdom on May 1, 2001 and was assigned Accession no. 01050118. In accordance with the "Statement of Availability of Biological Deposits", these cell lines will be maintained at the ECACC during the pendency of this application or any utility application filed there off of and during the term of any patent issuing therefrom in accordance with the rules of the United States Patent and Trademark Office which allows access to the Patent Office during the pendency of the application.

Early investigation by the inventors of the characteristics of SC101 demonstrated that the antibody caused the death of tumour cell-lines in suspension. The inventors have now found that the antibody causes the specific onset of apoptosis or programmed cell-death in colorectal tumour and leukaemia cell-lines and cells derived from disaggregated tumour tissue. Several groups including Terada and Nakanuma, Pathol. Int., 46, 764-770 (1996); Terada and Nakanuma, American J. Pathol., 146, 67-74 (1995); Iwata et al., J. Pathol., 179, 403-408 (1996); Yamada et al., Anticancer Research, 16, 735-740 (1996) have previously used anti-Lewis$^Y$ antibodies to characterise apoptotic cells; these results suggested that Lewis$^Y$ was a marker of apoptosis and predominantly over-expressed on dying cells. These findings do not explain why the majority of viable tumour cells also express this hapten or why a member (e.g. an antibody) which binds to Lewis$^Y$ and Lewis$^b$ should induce apoptosis.

Recognition of normal. tissue by the SC101 antibody is, surprisingly, minimal compared to tumour cells thereby making the antibody an effective anti-cancer agent. Since the Lewis$^Y$ and Lewis$^b$ antigens are expressed on tumour cells and also on normal cells, this finding was contrary to expectation of the art. The minimal binding of the SC101 antibody to normal tissues has the advantage in that a higher dose of the antibody can be used in the treatment of patients whilst avoiding any risk of toxicity to non-cancerous cells.

As used herein, references to "SC101" and "692" includes sequences which show substantial homology with SC101 and/or 692. Preferably, the degree of homology between SC101/692 complementarity determining regions (CDRs) and the CDRs of other antibodies will be at least 60%, more preferably 70%, further preferably 80%, even more preferably 90% or most preferably 95%.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87: 2264-2268, modified as in Karlin and Altschul (1993) Proc. Natl. Acad. Sci. USA 90: 5873-5877. The NBLAST and XBLAST programs of Altschul, et al. (1990) J. Mol. Biol. 215: 403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25: 3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov.

Another example of a mathematical algorithm utilised for the comparison of sequences is the algorithm of Myers & Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis & Robotti (1994) Comput. Appl. Biosci., 10: 3-5; and FASTA described in Pearson & Lipman (1988) Proc. Natl. Acad. Sci. 85: 2444-8. Within FASTA, ktup is a control option that sets the sensitivity and speed of the search.

Where high degrees of sequence identity are present there will be relatively few differences in amino acid sequence. Thus for example they may be less than 20, less than 10, or even less than 5 differences.

The present inventors have shown that SC101 and fragments and derivatives thereof can be used as cancer therapeutics to inhibit the growth or induce apoptosis of tumour cells as exemplified by the inhibition of growth of tumour cell lines, apoptosis of tumour cell lines and in vivo inhibition of tumour xenografts in nude mice (see the Examples) Accordingly the invention further provides the use of naked "fragments" or "derivatives" of SC101 or other polypeptides of the "SC101" family which bind to both Lewis$^Y$ and Lewis$^b$ epitopes in the preparation of an agent for treating cancer. A preferred group of fragments are those which include all or part of the CDR regions of monoclonal antibody SC101.

The binding member may comprise one or more of the CDRs of the antibody, or a fragment thereof, produced by the cell line deposited as ECACC Accession No. 01050118.

The binding member may be the antibody produced by the cell line deposited as ECACC Accession No. 01050118, or a fragment or derivative thereof.

A fragment of SC101 or of a polypeptide of the SC101 family generally means a stretch of amino acid residues of at least 5 to 7 contiguous amino acids. Often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

A "derivative" of SC101 or of a polypeptide of the SC101 family, or of a fragment of SC101 family polypeptide, means a polypeptide modified by varying the amino acid sequence of the protein, e.g. by manipulation of the nucleic acid encoding the protein or by altering the protein itself. Such derivatives of the natural amino acid sequence may involve insertion, addition, deletion and/or substitution of one or more amino acids, while providing a peptide capable of inducing an anti-tumour T-cell response.

Preferably such derivatives involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

The present invention further provides products comprising a naked binding member, which binds to both Lewis$^Y$ and Lewis$^b$ haptens, and an active agent as a combined preparation for simultaneous, separate or sequential use in the treatment of cancer. Preferably, the products contain a naked binding member, which binds to both Lewis$^Y$ and Lewis$^b$ haptens, and an active agent as a combined preparation for simultaneous, separate or sequential use in the treatment of cancer. Active agents may include chempotherapeutic agents including, Doxorubicin, taxol, 5-Fluorouracil (5 FU), Leucovorin, Irinotecan, Mitomycin C, Oxaliplatin, Raltitrexed, Tamoxifen and Cisplatin which may operate synergistically with the binding member of the present invention. Other active agents may include suitable doses of pain relief drugs such as non-steroidal anti-inflammatory drugs (e.g. aspirin, paracetamol, ibuprofen or ketoprofen) or opitates such as morphine, or anti-emetics.

The ability of the binding member to synergise with an active agent to enhance tumour killing may not be due to immune effector mechanisms but rather may be a direct consequence of the binding member binding to cell surface bound glycoproteins.

The binding member of the invention may carry a detectable label.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not after the binding specificity of antibodies produced.

As antibodies can be modified in a number of ways, the term "antibody" should be construed as covering any binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

A further aspect of the invention provides an antibody produced by the cell line deposited as ECACC Accession No. 01050118.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., *Nature* 341: 544-546 (1989)) which consists of a VH domain; (v) isolated CDR regions; (vi) F(ab') 2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., *Science* 242: 423-426 (1988); Huston et al., *PNAS USA* 85: 5879-5883 (1988)); (viii) bispecific single chain Fv dimers (PCT/US92/09965) and (ix)"diabodies", multivalent or multispecific fragments constructed by gene fusion (WO94/13804; P. Hollinger et al., *Proc. Natl. Acad. Sci. USA* 90: 6444-6448 (1993)).

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of monoclonal antibody SC101 and the constant region of a human antibody. Thus the binding member may comprise a human constant region.

The variable region other than the hypervariable region may also be derived from the variable region of a human antibody. The variable region of the antibody outside of the hypervariable region may also be derived from monoclonal antibody SC101. In such case, the entire variable region is derived from murine monoclonal antibody SC101 and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

The binding member of the first aspect of the invention binds to Lewis$^Y$ (Fucα 1-2Galβ 1-4 (Fucα 1-3) GlcNAc) and Lewis$^b$ (Fuc1-2Galβ1-3 (Fucα 1-4) GINAc) haptens which may be in extended or non-extended form. The extended forms of Lewis$^Y$ and Lewis$^b$ are as follows:

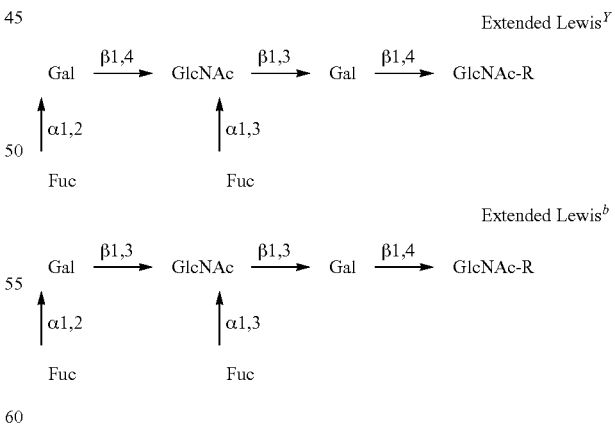

"Treatment" includes any regime that can benefit a human or non-human animal. The treatment may be in respect of an existing condition or may be prophylactic (preventative treatment).

"Treatment of cancer" includes treatment of conditions caused by cancerous growth and includes the treatment of neoplastic growths or tumours. Tumours may be benign or malignant. Tumours may include colorectal, breast, ovarian, gastric, lung tumours, liver, skin, myeloid (e.g. bone marrow) tumours. Treatment may also be in respect of cancerous tissues or cell lines including, but not limited to, leukaemic cells.

The binding member may, upon binding to Lewis$^Y$ and Lewis$^b$ haptens present on cancerous cells or tissues, including tumour and non-tumour cells, induce apoptosis of cells and inhibit the growth of cells.

Apoptosis is the process by which a cell actively commits suicide. It is now well recognized that apoptosis is essential in many aspects of normal development and is required for maintaining tissue homeostasis. Cell death by suicide, sometimes referred to as programmed cell death, is needed to destroy cells that represent a threat to the integrity of the organism. There are two different mechanisms by which a cell commits suicide by apoptosis. One is triggered by signals arising from within the cell, the other by external signals (e.g. molecules) which bind to receptors at the cell surface.

Binding members of the present invention may be administered to a patient in need of treatment via any suitable route, usually by injection into the bloodstream. The precise dose will depend upon a number of factors, including the precise nature of the member (e.g. whole antibody, fragment or diabody), and the nature of the detectable label attached to the member.

Binding members of the present invention will usually be administered in the form of a pharmaceutical composition, which may comprise at least one component in addition to the binding member.

Thus a further aspect provides pharmaceutical compositions according to the present invention, and for use in accordance with the present invention. Pharmaceutical compositions may comprise, in addition to active ingredient, a pharmaceutical acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

The formulation may be a liquid, for example, a physiologic salt solution containing non-phosphate buffer at pH 6.8-7.6, or a lyophilised powder.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing cancer and in the prevention of the recurrence of cancer after initial treatment or surgery. Examples of the techniques and protocols mentioned above can be found in Remington's Pharmaceutical Sciences, 16th edition, Oslo, A. (ed), 1980.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m$^2$ of antibody provides a serum concentration of approximately 20 nM for approximately eight days As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of Lewis$^{Y/b}$ haptens.

Some suitable routes of administration include intravenous, subcutaneous and intramuscular administration. Intravenous administration is preferred.

It is envisaged that injections (intravenous) will be the primary route for therapeutic administration of the compositions although delivery through a catheter or other surgical tubing is also used. Liquid formulations may be utilised after reconstitution from powder formulations.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22 (1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12: 98-105, 1982). Liposomes containing the polypeptides are prepared by well-known methods: DE 3,218, 121 A; Epstein et al, PNAS USA, 82: 3688-3692, 1985; Hwang et al, PNAS USA, 77: 4030-4034, 1980; EP-A-0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage.

The composition may be administered in a localised manner to a tumour site or other desired site or may be delivered in a manner in which it targets tumour or other cells.

The dose of the composition will be dependent upon the properties of the binding member, e.g. its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 300, μg of antibody per patient per administration are preferred, although dosages may range from about 10 μg to 6 mg per dose. Different dosages are utilised during a series of sequential inoculations; the practitioner may administer an initial inoculation and then boost with relatively smaller doses of antibody.

This invention is also directed to optimise immunisation schedules for enhancing a protective immune response against cancer.

The binding members of the present invention may be generated wholly or partly by chemical synthesis. The binding members can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding member according to the present invention is to express nucleic acid encoding it, by use of nucleic acid in an expression system.

Thus the present invention further provides the use of an isolated nucleic acid encoding a naked binding member which binds to both Lewis$^Y$ and Lewis$^b$ haptens in the preparation of an agent for treating cancer.

The present invention also provides a pharmaceutical composition for the treatment of cancer, the composition comprising a naked binding member which binds to both Lewis$^Y$ and Lewis$^b$ haptens.

Nucleic acid includes DNA and RNA. In a preferred aspect, the present invention provides a nucleic acid which codes for a binding member of the invention as defined above. The skilled person will be able to determine substitutions, deletions and/or additions to such nucleic acids which will still provide a binding member of the present invention.

Nucleic acid sequences encoding a binding member in accordance with the present invention can be readily prepared by the skilled person using the information and references contained herein and techniques known in the art (for example, see Sambrook, Fritsch and Maniatis, "Molecular Cloning", A Laboratory Manual, Cold Spring Harbor Laboratory Press, 1989, and Ausubel et al, Short Protocols in Molecular Biology, John Wiley and Sons, 1992), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding antibody fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The present invention also provides constructs in the form of plasmids, vectors, transcription or expression cassettes which comprise at least one nucleic acid as described above.

The present invention also provides a recombinant host cell which comprises one or more constructs as above. Expression may conveniently be achieved by culturing under appropriate conditions recombinant host cells containing the nucleic acid. Following production by expression a specific binding member may be isolated and/or purified using any suitable technique, then used as appropriate.

Binding members encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antibody fragments in prokaryotic cells such as E. coli is well established in the art. For a review, see for example Plückthun, *Bio/Technology* 9: 545-551 (1991). Expression in eukaryotic cells in culture is also available to those skilled in the art as an option for production of a binding member, see for recent review, for example Reff, *Curr. Opinion Biotech.* 4: 573-576 (1993); Trill et al., *Curr. Opinion Biotech.* 6: 553-560 (1995).

Suitable vectors can be chosen or constructed, containing appropriate regulator sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Sambrook et al., *Molecular Cloning: A Laboratory Manual:* 2nd Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., *Short Protocols in Molecular Biology,* 2"d Edition, John Wiley & Sons (1992).

The nucleic acid may be introduced into a host cell by any suitable means.

The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells under conditions for expression of the gene.

The nucleic acid of the invention may be integrated into the genome (e.g. chromosome) of the host cell. Integration may be promoted by inclusion of sequences which promote recombination with the genome in accordance with standard techniques. The nucleic acid may be on an extra-chromosomal vector within the cell, or otherwise identifiably heterologous or foreign to the cell.

The present invention further provides a screening method comprising the step of screening a library of candidate agents for the ability to inhibit the binding of a naked binding member, as defined according to the first aspect of the invention, to Lewis$^y$ and Lewis$^b$ haptens.

The screening method may comprise any of the following steps:

1. providing a naked binding member with the ability to bind to Lewis$^Y$ and Lewis$^b$ haptens;
2. providing candidate drugs;
3. screening the candidate drugs by contacting the naked binding member with one of the candidate drugs and determining the extent to which the candidate drug inhibits binding of the naked binding member to Lewis$^Y$ and Lewis$^b$ haptens.

The screening method may additionally comprise the step of selecting an agent which has the ability to inhibit the binding of the naked binding member to Lewis$^Y$ and Lewis$^b$ haptens, and optionally modifying the agent to optimise the agent for administration as a medicament.

The present invention further provides the use of an agent identified by the screening method of the present invention in the manufacture of a medicament for the treatment of cancer.

Preferred features of each aspect of the invention are as for each of the other aspects mutatis mutandis.

The invention will now be described further in the following non-limiting examples. Reference is made to the accompanying drawings in which:

FIG. 1 Thin layer chromatographs showing immunostaining of extended Lewis$^b$ (lane 1), extended Lewis$^y$ (lane 2), H type 1 chain (lane 3), H type 2 chain (lane 4) Lewis$^x$ (lane 5), Lewis$^b$ (lane 6) and Lewis$^y$ (lane 7). Plates are stained with either Orcinol panel A or Mabs SC101/23 panel B, Mab SC101/29 panel C, Mab SC101/33 panel D, Mab SC101/42 panel E and Mab C14 panel F.

Figure 2:
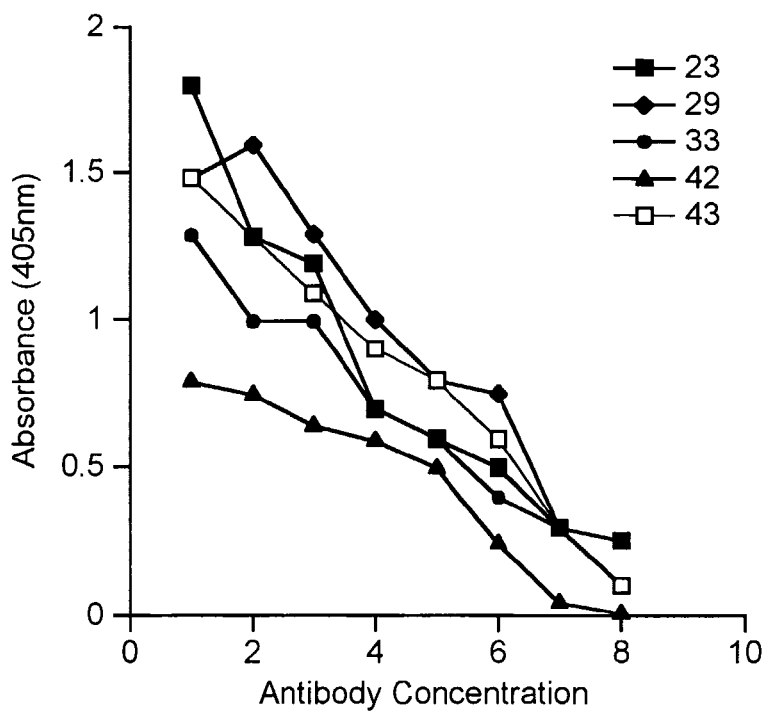
Figure 2:
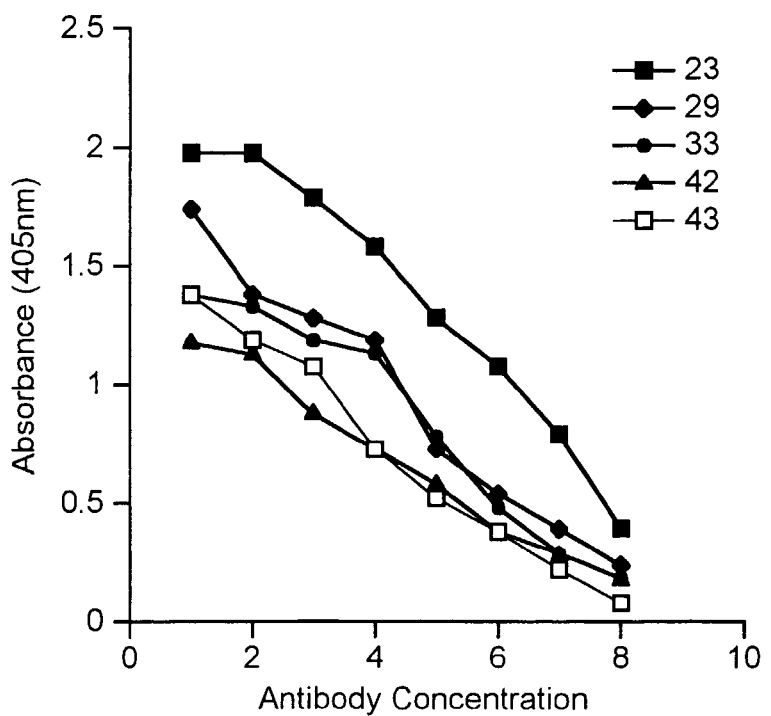

FIG. 2 ELISA analysis of SCIOI binding to haptens. Binding of SC101/23 (○), SC101/29 (●), SC101/33 (▽) SC101/42 (□) and SC101/43 (■) to a) Lewis$^Y$ and b) Lewis$^b$ haptens as determined by ELISA.

Figure 3:
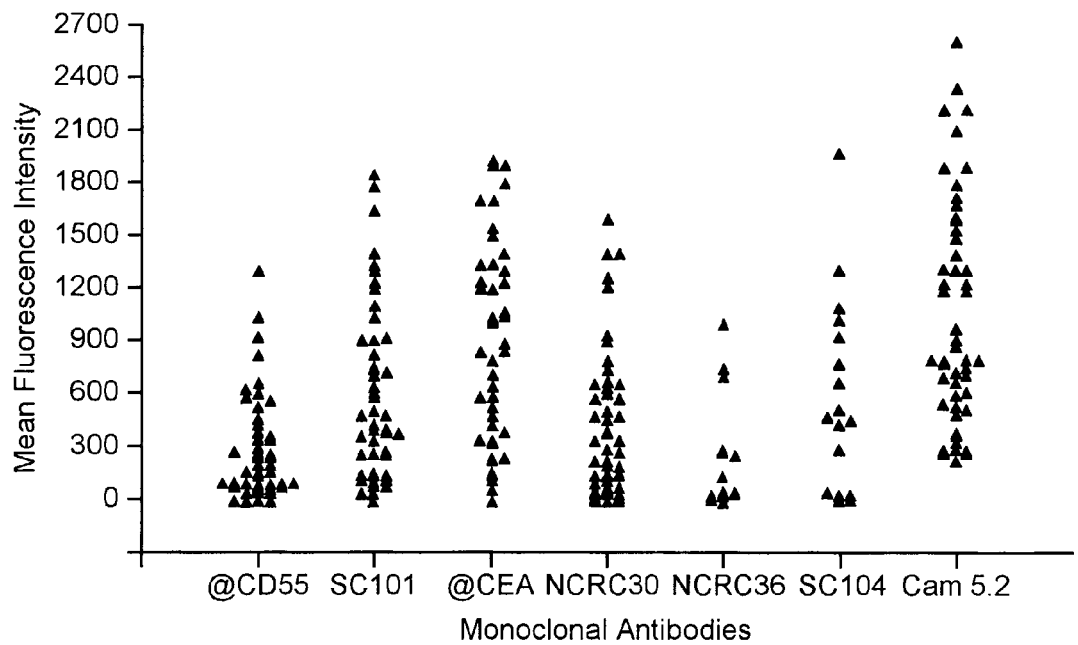

FIG. 3 A graph demonstrating binding of monoclonal antibodies to freshly disaggregated colorectal tumour cells, as assayed by indirect immunofluorescence and analysed by flow cytometry. Each point refers to the mean fluorescence for an individual tumour. NCRC30, NCRC36 and SC104 (provided by Scancell Limited) are included as positive controls to demonstate integrity of enzyme disaggregation.

Figure 4:
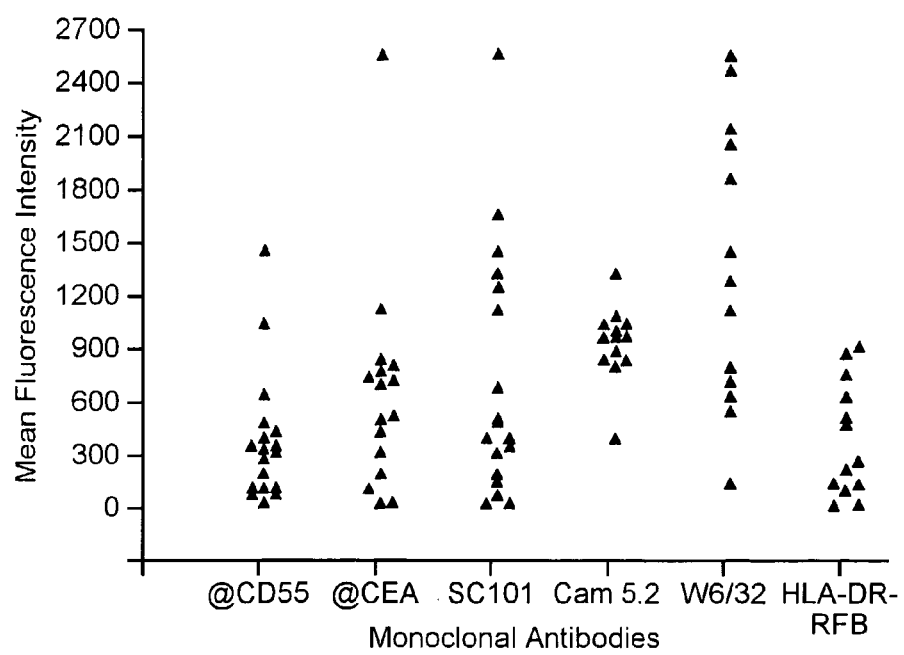

FIG. 4 A graph demonstrating binding of monoclonal antibodies to freshly disaggregated gastric tumour cells, as assayed by indirect immunofluorescence and analysed by flow cytometry. Each point refers to the mean fluorescence for an individual tumour. HLA/ABC, HLA-DR-AFB and w6/32 (Serotech) are included as positive controls to demonstate integrity of enzyme disaggregation.

Figure 5:
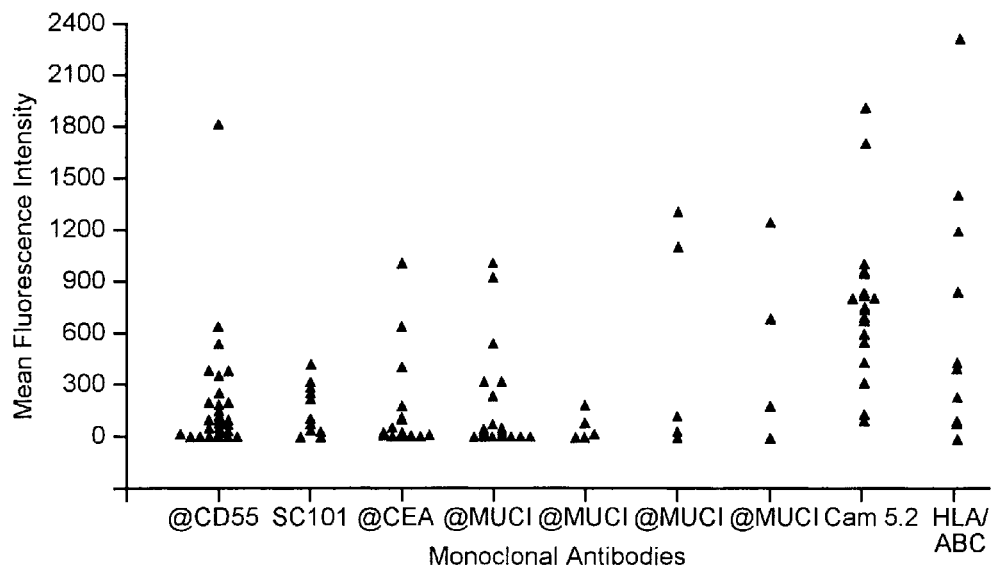

FIG. 5 A graph demonstrating binding of monoclonal antibodies to freshly disaggregated ovarian tumour cells, as assayed by indirect immunofluorescence and analysed by flow cytometry. Each point refers to the mean fluorescence for an individual tumour.

Figure 6:
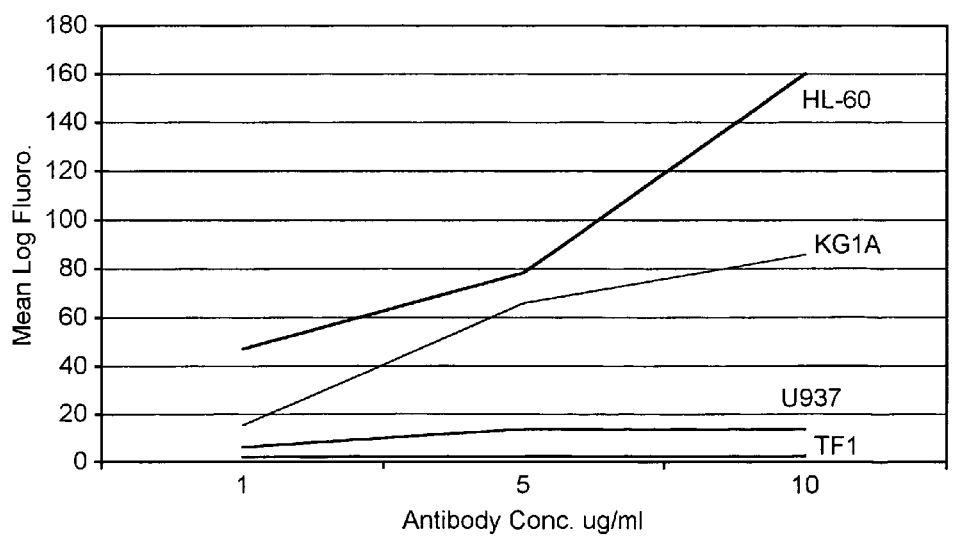

FIG. 6 A graph demonstrating binding of SC101/29 to a panel of acute myeloid leukaemic (AML) cell lines (HL-60, KG1A, U937, TF1 (obtained from ECACC)). Cells were stained by indirect immunofluorescence and analysed by flow cytometry. Results are expressed as a mean linear fluorescence for each cell line.

Figure 7:
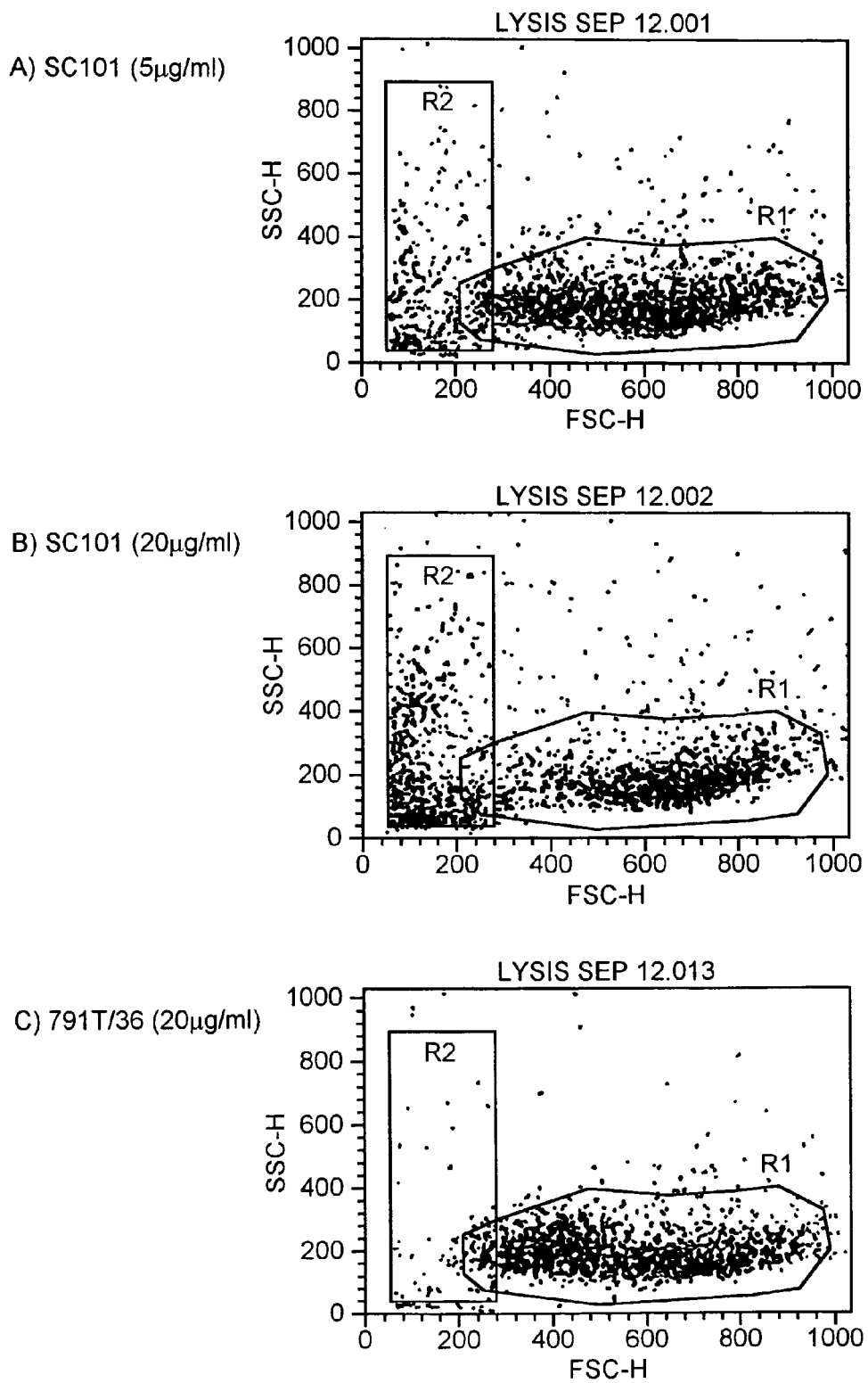

FIG. 7 Scatter diagrams demonstrating size (forward scatter, FSCH) and granularity (side scatter, SSCH) of colorectal tumour cell line, C170, exposed to SC101/29 or control 791T/36 antibody. Cells were analysed for size and granularity by flow cytometric analysis of forward and side scatter. R1 gate defines viable healthy cells. R2 gate defines dying cells with reduced size and granularity.

Figure 8:
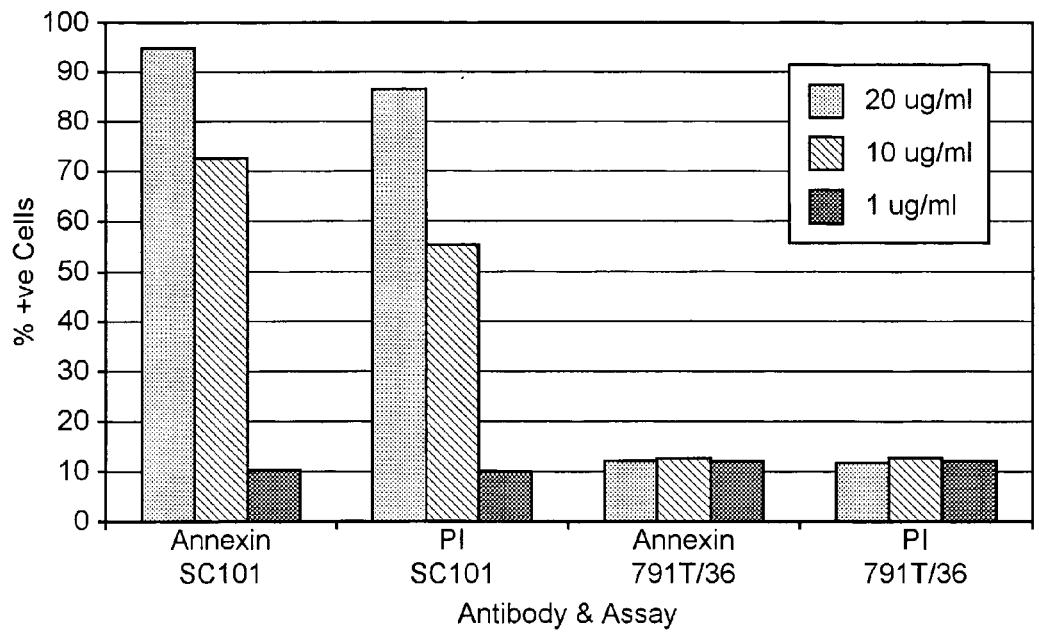

FIG. 8 A histogram demonstrating the effect of SC101/29, or control 791T/36 antibody, on C170 tumour cells. Cells were stained with FITC labelled Annexin and propidium iodide and then analysed by dual colour flow cytometry. A-C170 colorectal tumour cells, B-HT29 colorectal tumour cells C-HL60 myeloid leukaemic cells.

FIG. 9 Graphs demonstrating in vitro inhibition of cell growth. Tumour cell lines a) C170 colorectal tumour cells b) HL-60 myeloid leukaemic cells were exposed to SC101/29 or control 791T/36 monoclonal antibody. The number of cells was determined by crystal violet staining and optical density reading at 550 nm.

Figure 10:
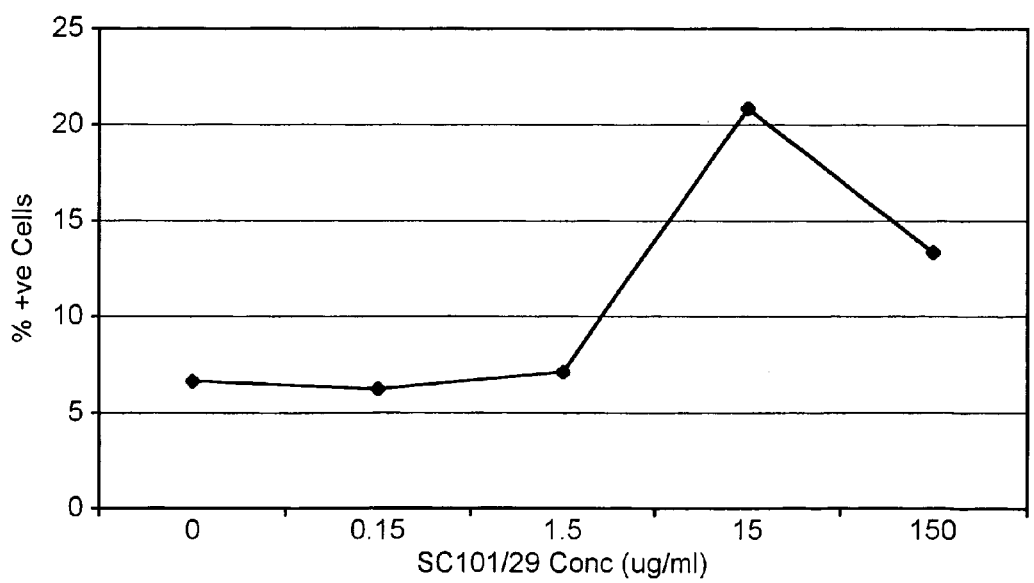

FIG. 10 A graph demonstrating the effect of SC101/29 antibody on cell growth. HL-60 cells were incubated with SC101/29 antibody for 1 hr at room temperature and then the cells were stained with phycoerythrin conjugated Apo2.7 mouse monoclonal antibody. Stained cells were enumerated by flow cytometry. HL60 myeloid leukaemic cells undergo apoptosis as measured by Apo2.7 staining when exposed to SC101/29 monoclonal antibody.

Figure 11:
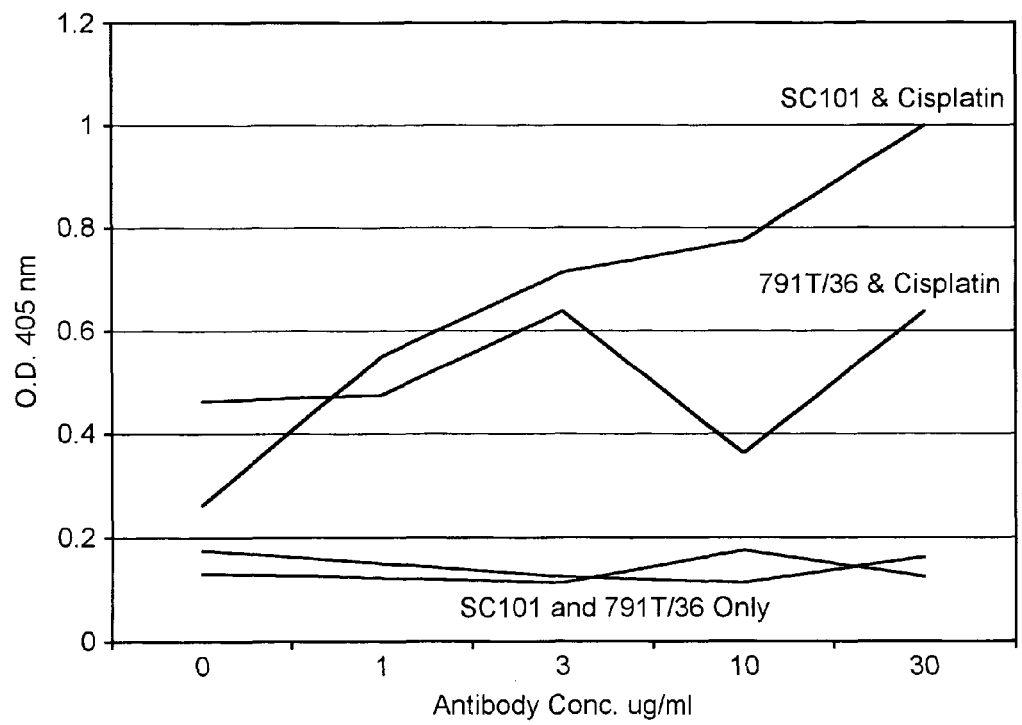

FIG. 11 A graph demonstrating the effect of SC101/29 and cisplatin on cells. Colorectal tumour cells were treated with various dilutions of SC101/29 or control 791T/36 antibody. The cultures left overnight in culture medium with or without cisplatin. The cultures were tested for the presence of fragmented DNA by a CytoDeath ELISA (Roche). The results were recorded by optical Density measurements at 405 nm.

Figure 12:
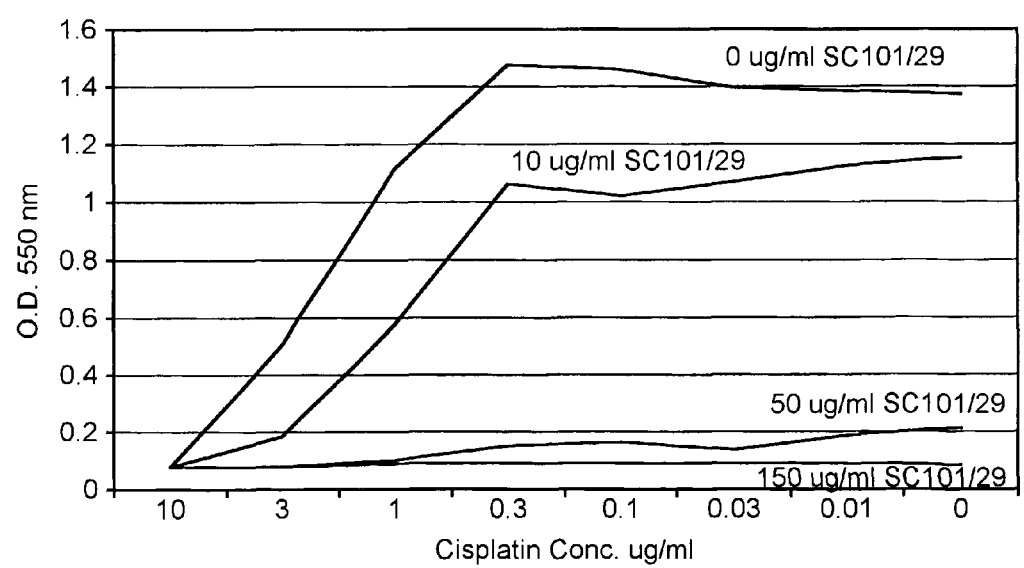

FIG. 12 A graph demonstrating the effect of cisplatin and SC101/29 on cell viability. Colorectal tumour cells were exposed to cisplatin and then SC101/29 or control 791 T/36 antibody was added. The cells were left for 4 days when the number of viable cells was determined by crystal violet staining and optical density reading at 550 nm.

Figure 13:
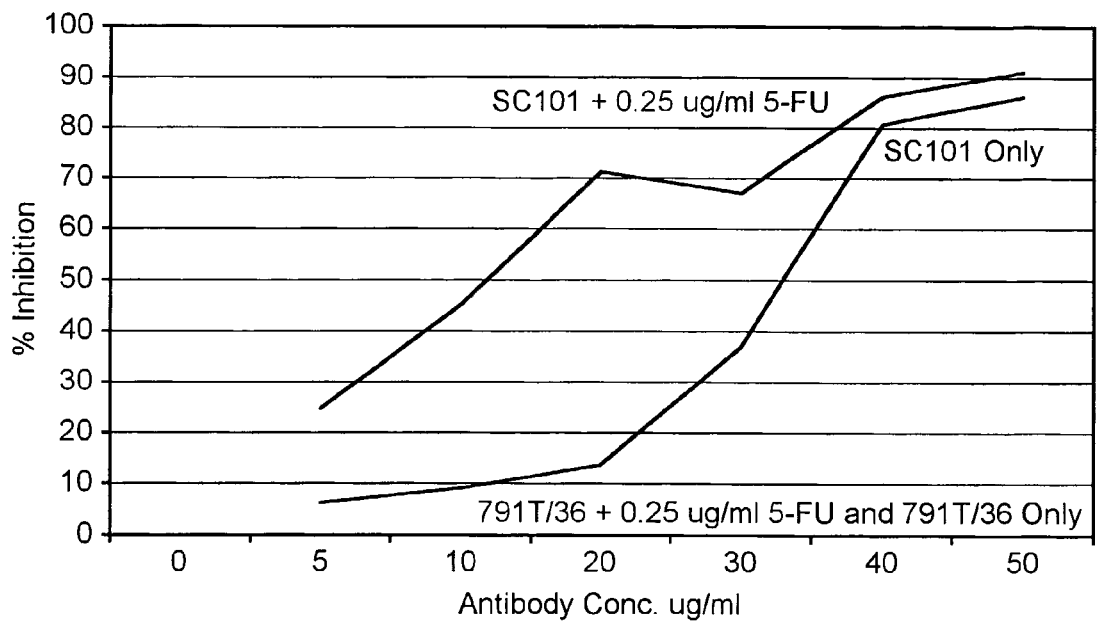

FIG. 13 A graph demonstrating the effect of 5 Fluorouracil and SC101/29 antibody on cells. C170 cells were exposed to SC101/29 or control 791T/36 antibody and 5 FU. The number of cells was determined by crystal violet staining and optical density reading at 550 nm.

Figure 14:
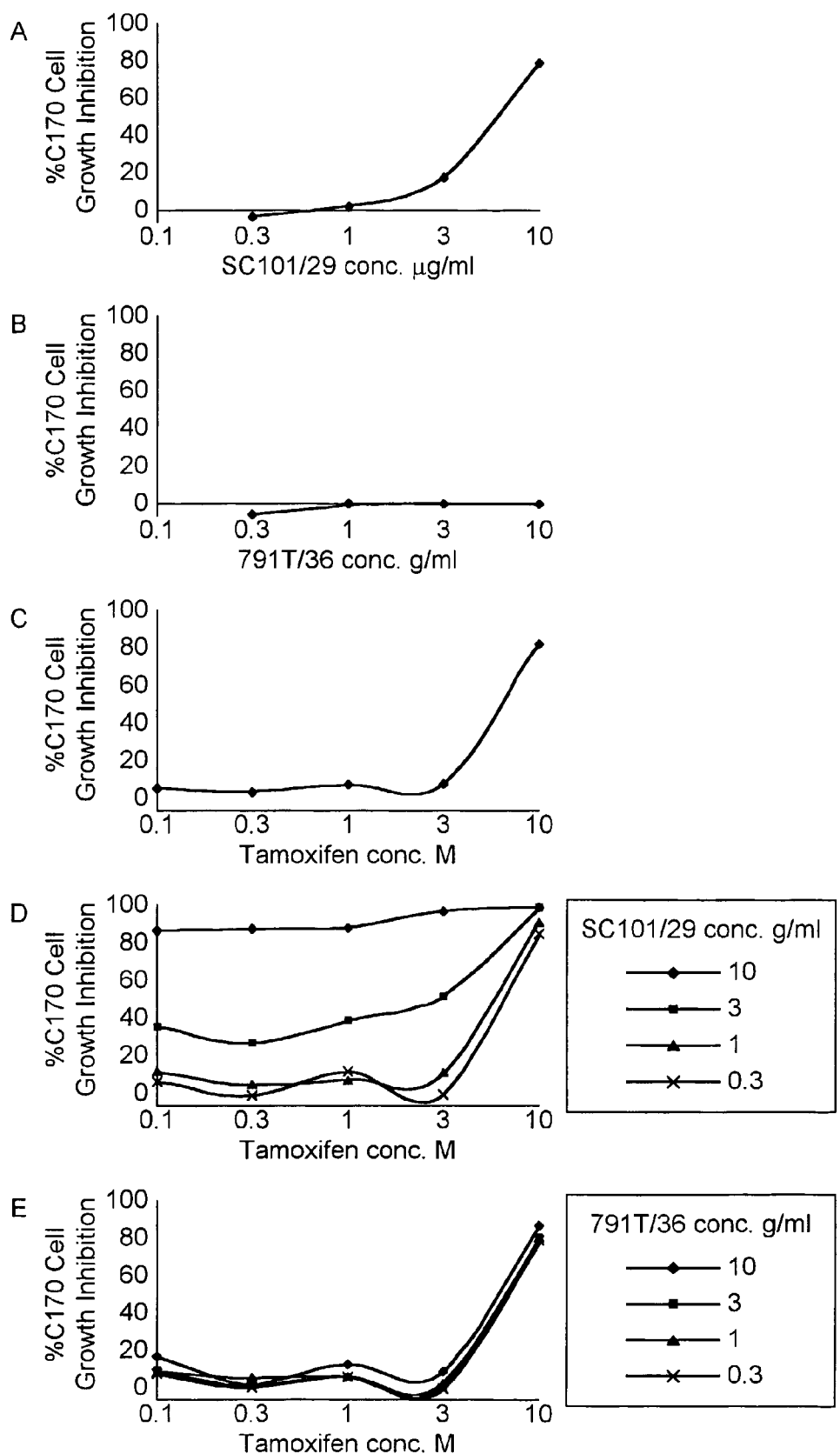

FIG. 14 A graph demonstrating the effect of Tamoxifen and SC101/29 on C170 colorectal cells. C170 cells were exposed to SC101/29 or control 791T/36 antibody or Tamoxifen or combinations thereof.

Figure 15:
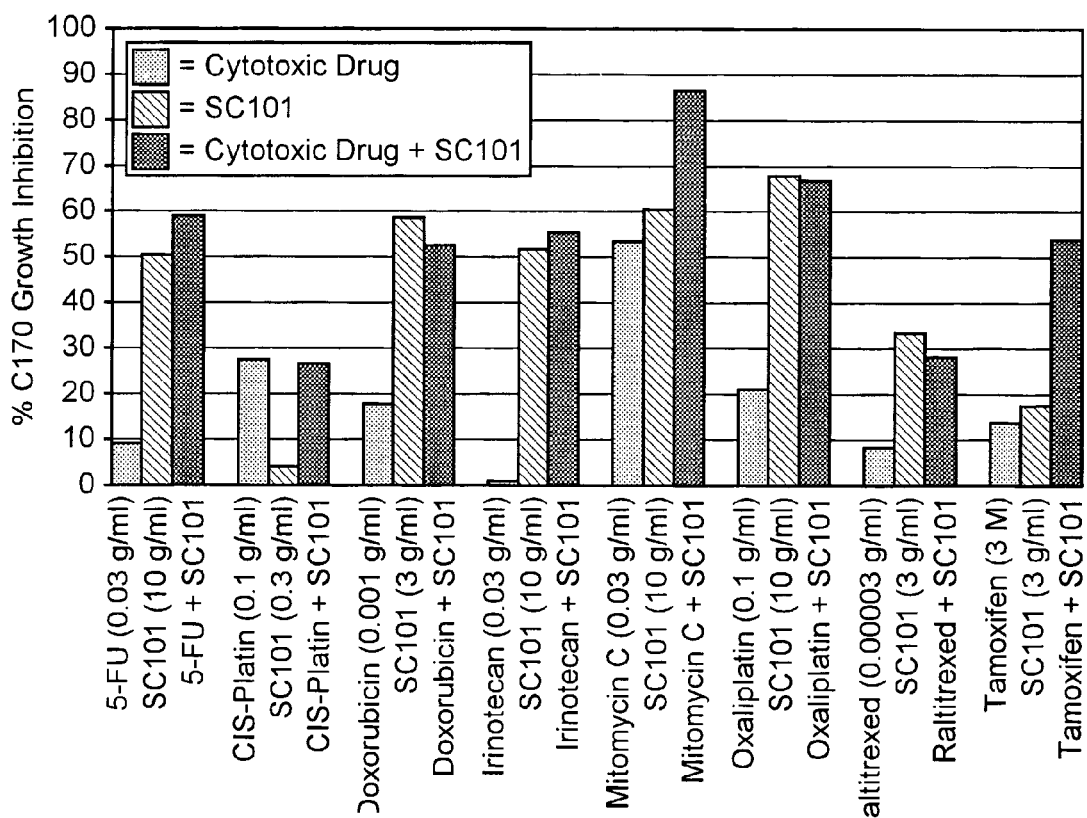

FIG. 15 A graph demonstrating the effects of 5-FU, Cisplatin, Doxorubicin, Irinotecan, Mitomycin C, Oxaliplatin, Raltitrexed and Tamoxifen on C170 cells either alone or in combination with SC101/29 antibody, or with SC101/29 antibody alone.

Figure 16:
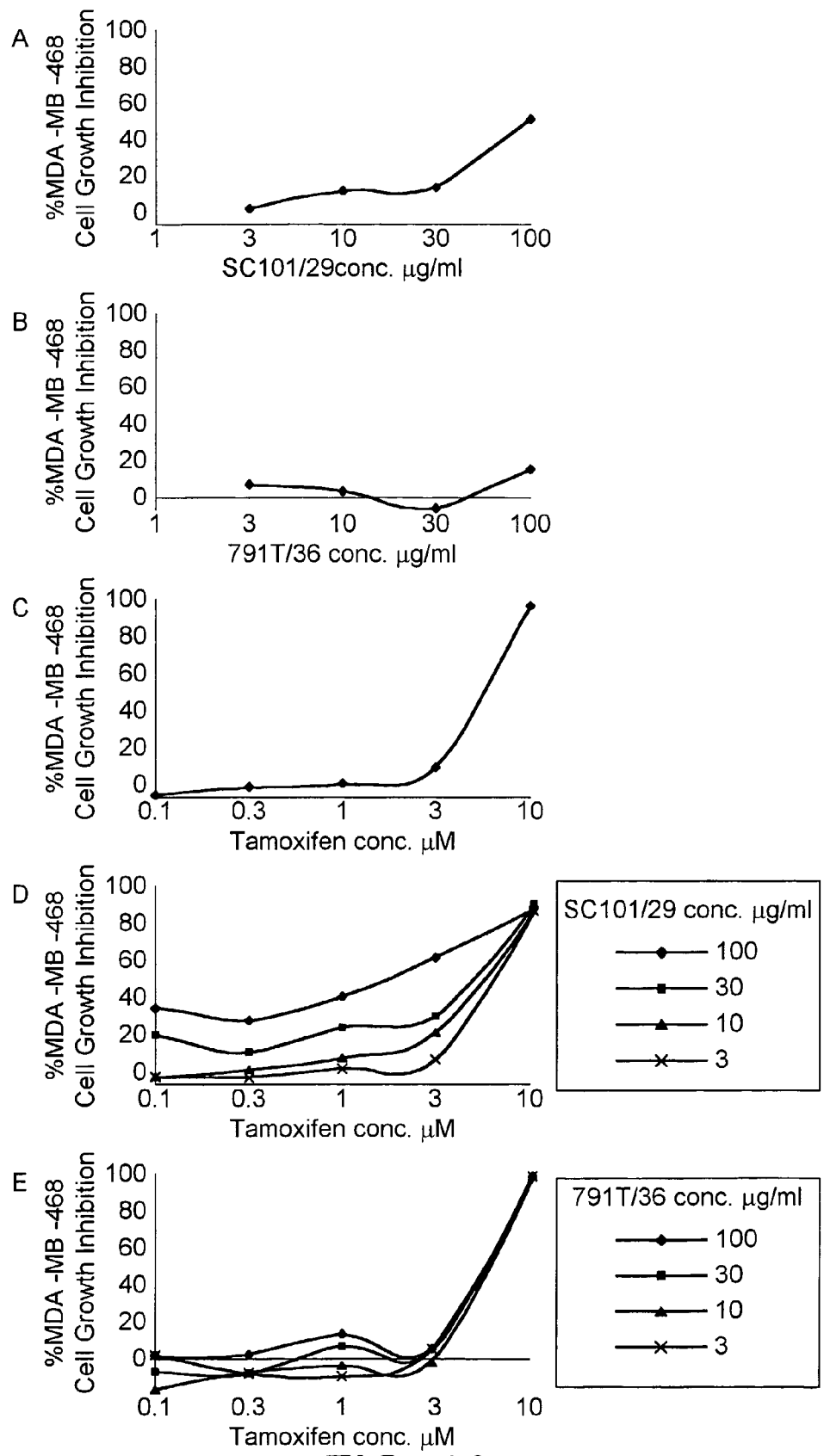

FIG. 16 A graph demonstrating the effect of Tamoxifen and SC101/29 on MDA-MB-468 cells exposed to SC101/29 or control antibodies alone or in combination with Tamoxifen.

Figure 17:
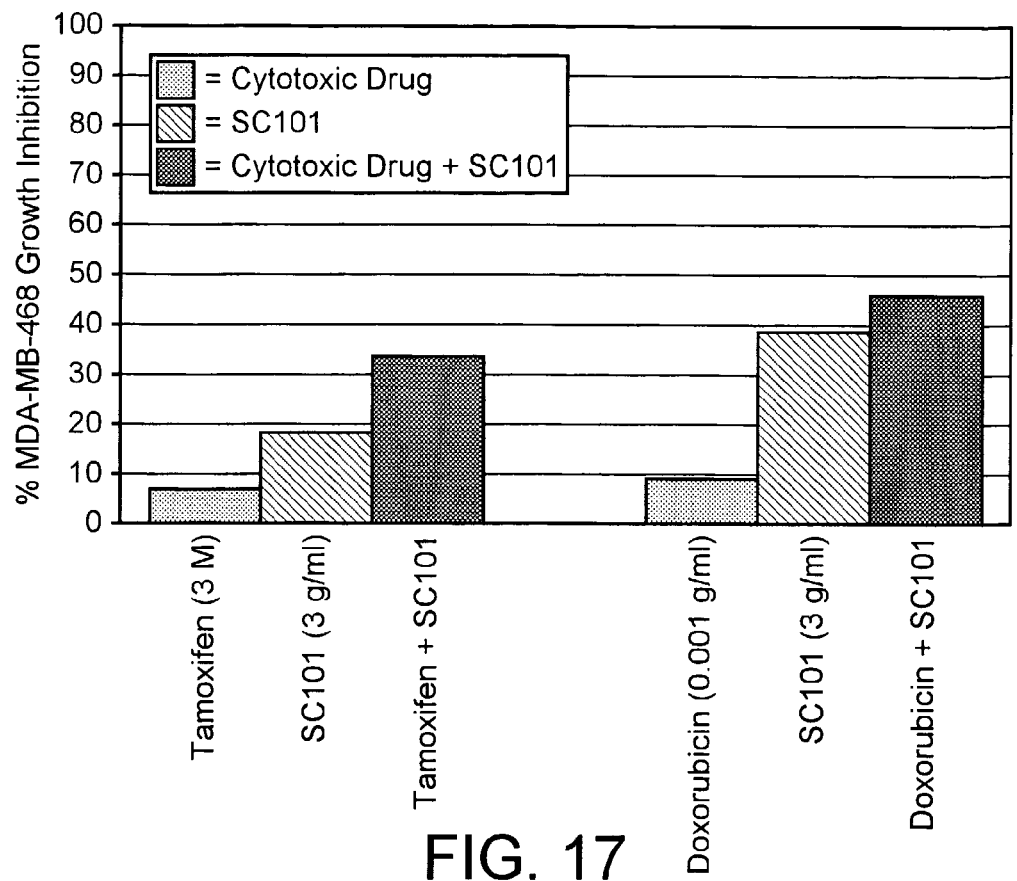

FIG. 17 A graph demonstrating the effects of Tamoxifen and Doxorubicin on MDA-MB-468 breast cells either alone or in combination with SC101/29 antibody or exposed to SC101/29 antibody alone.

Figure 18:
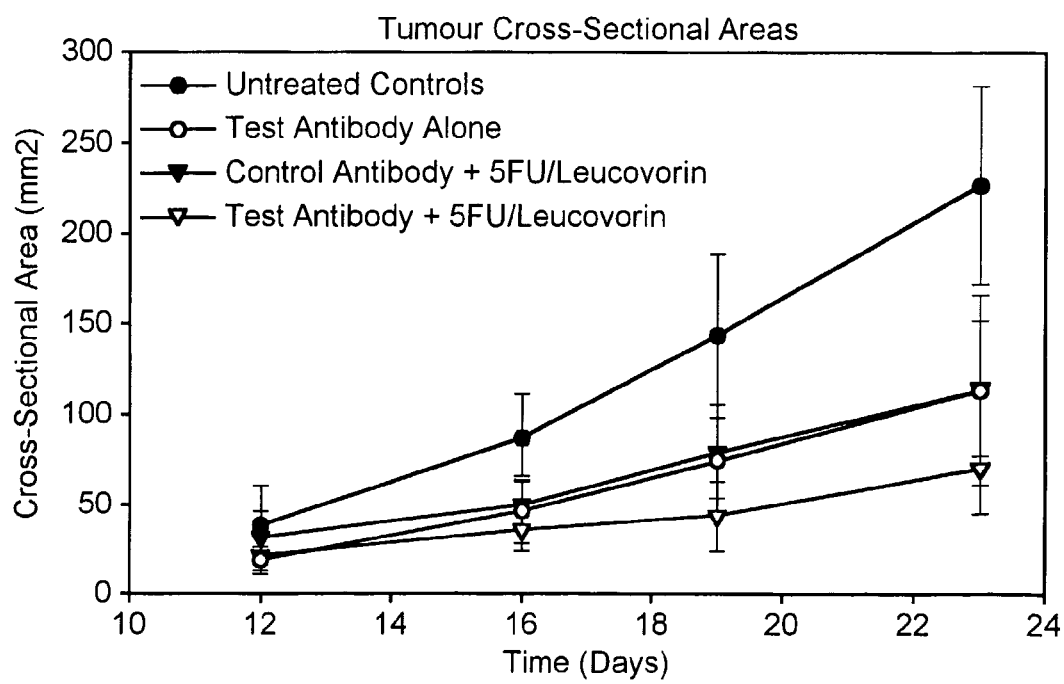

FIG. 18 A graph demonstrating the effect of SC101, 5 FU/leucovorin and a combination of SC1010 and 5 FU/leucovorin on the growth of C170 xenografts growing in nude mice. Growth of C170 xenografts was measured at days 12, 16, 19 and 23 by measurement of cross-sectional area (mm$^2$) when animals were treated with either SC101 ip (0.2 mg) (○), control antibody ip (0.2 mg) and 5 FU/leucovorin (12.5 mg/Kg iv) (∇) or SC101 ip (0.2 mg) and 5 FU/leucovorin (12.5 mg/Kg iv, ∇) on days 1, 3, 5, 7, 21, 22.

Figure 19:
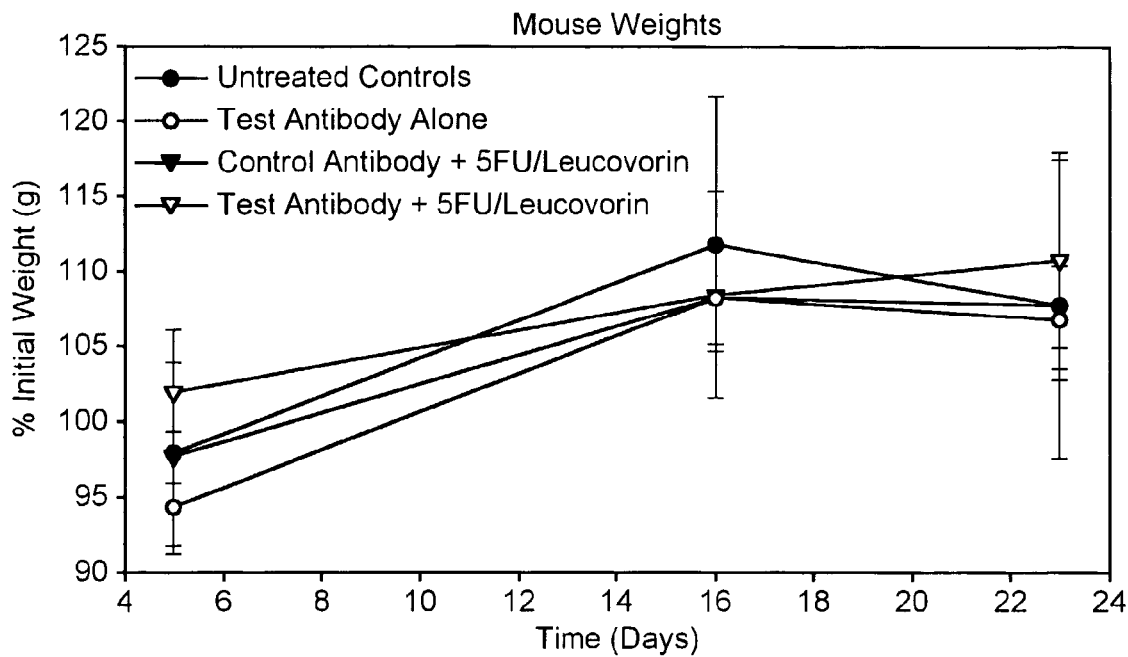

FIG. 19 A graph demonstrating the effect of SC101, 5 FU/leucovorin or the combination of SC101 and 5 FU/leucovorin on the weights of mice. Animals were weighed on days 12, 16, 19 and 23 following treatment with SC101 ip (0.2 mg) (○), control antibody ip (0.2 mg) and 5 FU/leucovorin (12.5 mg/Kg iv) (∇) or SC101 ip (0.2 mg) and 5 FU/leucovorin (12.5 mg/Kg iv, ∇) on days 1, 3, 5, 7, 21, 22.

Figure 20:
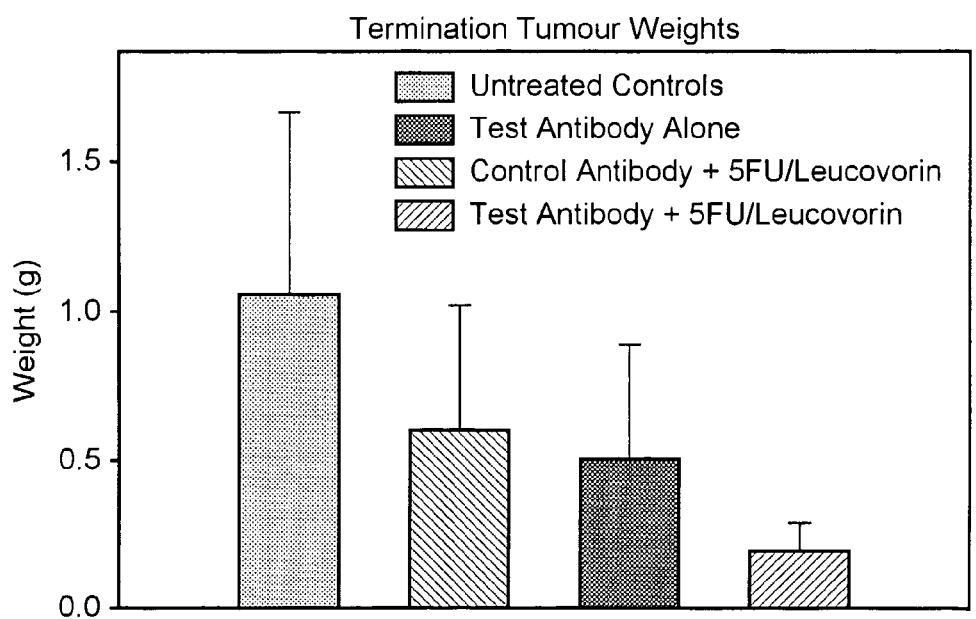

FIG. 20 A histogram demonstrating the effect of SC101, 5 FU/leucovorin or the combination of SC101 and 5 FU on the final tumour weights of C170 xenografts grown in nude mice. animals were treated with either SC101 ip (0.2 mg) (○), control antibody ip (0.2 mg) and 5 FU/leucovorin (12.5 mg/Kg iv) (Δ) or SC101 ip (0.2 mg) and 5 FU/leucovorin (12.5 mg/Kg iv, Δ) on days 1, 3, 5, 7, 21, 22.

The invention is now described with reference to the following non-limiting examples;

EXAMPLE 1

Binding Studies Using SC101 Monoclonal Antibody

Methods
Binding to Carbohydrates Separated by Thin Layer Chromatography

Purified glycolipid standards containing Lewis$^b$, Lewis$^Y$, trifucosyl Lewis$^b$, trifucosyl Lewis$^Y$, H type 1 chain, H type 2 chain, and Lewis$^X$ were spotted on the TLC plates were run in a solvent system of Chloroform:methanol:0.2% Calcium chloride: 50:40:10. The plates were then blocked with 5% BSA and then incubated with either Orcinol, panel A or Mabs SC101/23 panel B, Mab SC101/29 panel C, Mab SC101/33 panel D, Mab SC101/42 panel E and Mab C14 panel F. After washing the plates, they were incubated with rabbit anti-mouse IgG and IgM, followed by incubation with $^{125}$I labelled protein A. The bands were visualised by autoradiography.

Binding to Carbohydrates as Assayed by ELISA

Microtitre plates were coated with either purified Lewis$^b$ or Lewis$^Y$ glycolipids at (5 ug/ml) After blocking the plates with 5% bovine serum albumin diluted in phosphate buffered saline, purified monoclonal antibodies SC101/23, SC101/29, SC101/33, SC101/42 were added at different concentrations (0.15-20 μg/ml) followed by the additional of peroxidase conjugated goat anti-mouse IgG and IgM. Bound enzyme was detected by optical density reading at 490 nm.

Binding to Freshly Disaggregated Tumour Cells

Colorectal tumours were collected and disaggregated with collagenase (0.05%, Type IV) into highly viable single cell suspensions and assayed for binding with SC101 by indirect immunofluorescence where binding of SC101 was detected with a rabbit anti-mouse anti-serum conjugated to FITC. Stained cells were analysed for fluorescence by a FACS IV cell sorter. Fluoroescein fluorescence was excited at 488 nm and collected via a 10 nm band pass filter centred at 515 nm and adjusted to standard conditions using fluorochrome labelled latex beads. Fluorescence intensity is expressed as mean linear fluorescence (MLF), calculated by multiplying the contents of each channel by its channel number and dividing by the total number of cells in the distribution. The FACS IV is set to selectively analyse cells in the malignant cell size range. Each tumour was also stained using normal mouse Ig and the MLF in this control was subtracted from the values obtained with monoclonal antibody. However, the mean binding of normal mouse Ig was 50±25 and therefore tumours were only described as positively staining if the MLF exceeds 50±2s.d. i.e. 100. This was a conservative estimate as background of positively stained cells was calculated as the number of cells with a fluorescence that exceeded the value in which 95% of cells staining with normal mouse immunoglobulin were observed.

Disaggregation of solid tumours yields a mixed population of cells including red blood cells, lymphocytes, stromal cells, macrophages and endothelial cells. The percentage of epithelial cells, as measured by staining of cytokeratin with monoclonal antibody Cam 5.2, was only 22±13% (range 10-60). However, following forward angle light scatter gating to selectively analyse cells in the malignant cell size range 79±4% (range 69-86) of the cells analysed were epithelial. Furthermore the variation between tumours was considerably reduced.

The percentage of lymphocytes, as measured by staining with the monoclonal antibody F10-89-4 (kindly provided by Peter Beverley, Genera Institute), in the total nucleate population was 74±16 (range 40-90). This was considerably reduced to 5.5±5% (range 1-20) following FACS IV gating for malignant cell size. The percentage of stromal cells in the population of cells analysed in the malignant size range was 3.5±3% (range 1-13).

Although the percentage of non-epithelial cells in the forward light scatter gate was low and did not vary considerably between tumours (21±4%). This may have affected the mean linear fluorescence of particular tumours or if they failed to stain contributed to the heterogeneity of staining. Therefore only tumours in which >25% (i.e. 21±34% non epithelial cells) of the cells stained were described as positive.

Binding to Leukaemic Cell Lines $5 \times 10^4$ cells from well characterised myeloid leukaemic cell-lines were incubated with various dilutions of SC101 antibody and left for 1 hour on ice. Following extensive washing the cells were mixed with a FITC labelled anti-mouse conjugate for a further 30 minutes on ice. After washing for a second time the cells were fixed in proprietary cellfix and bound fluorescence measured by flow cytometry.

Binding to Normal Tissues

Binding of SC101 antibody to normal tissues was determined by indirect immunoperoxidase staining of post-mortem samples. Tissue sections (5 μm) of cryopreserved tumour and normal tissues were treated with 0.3% $H_2O_2$ in 0.1% $NaN_3$ for 15 min to inhibit endogenous peroxidase. This was followed by incubation at room temperature with 10% human serum and 1% BSA prepared in PBS, for 30 min, and then the mouse SC101 monoclonal antibodies were added at saturating levels which gave minimal non specific background staining for a further 30 min. The bound antibody was detected with rabbit anti-mouse Ig conjugated to peroxidase and following extensive washing the slides were stained with 0.05% diaminobenzidine and 0.01% $H_2O_2$ in 0.05M Tris-HCl, pH7.6 and counter stained with haematoxylin.

Results

A monoclonal antibody C14 was raised in mice against primary colorectal tumour cells. This antibody showed good tumour selectivity as it binds to a cell surface antigen over-expressed by a range of tumours and only present at low levels on normal cells. However C14 is an IgM antibody and of limited value for tumour therapy. An antiserum raised in rats to C14 was used to immunise mice and select 5 new IgG monoclonal antibodies. These monoclonal antibodies are referred to as SC101/23, SC101/29, SC101/33, SC101/42, SC101/43. These antibodies were shown to recognise extended and non-extended Lewis$^Y$ and Lewis$^b$ antigens but not Lewis$^x$ or H blood group antigen by thin layer chromatography (FIG. 1) and ELISA (FIG. 2).

FIG. 3 shows that SC101 the antigen recognised by SC101 shows a similar distribution to antigens, CD55, CEA and cytokeratin, recognised by antibodies NCRC30, NCRC36, SC104 and Cam 5.2. FIG. 4 shows that the antigen recognised by SC101 shows a similar distribution to antigens, CD55 and CEA, recognised by antibody HLA/DR, W6/32 and cam 52. FIG. 5 shows that the antigen recognised by SC101 shows a similar distribution to antigens CD55, CEA, MUC1 recognised by HLA/ABC and cam52.

Epithelial cells are known to express cytokeratin. These results show that as the majority of the tumours are cytokeratin positive, SC101 recognises cells of epithelial tumour origin.

Staining disaggregated tumour cells with SC101 antibody demonstrates that Lewis$^Y$ and Lewis$^b$ antigens are over-expressed by a wide variety of tumours including colorectal (FIG. 3), gastric (FIG. 4), ovarian (FIG. 5), breast, lung and myeloid leukaemia (FIG. 6).

TABLE 1

Binding of SC101 monoclonal antibodies to normal tissues

| TISSUES | Binding of SC101 to Tissues[1] |
|---|---|
| Rectum | No epithelial or stromal staining |
| Descending Colon | No epithelial or stromal staining |
| Proximal Colon | No epithelial or stromal staining |
| Ileum | No epithelial or stromal staining |
| Jejunum | Basement membrane of villious epithelium |
| Duodenum | Basement membrane staining of villi in selected Areas. Mucin staining in acini |
| Stomach | Mucin staining |
| Liver | Weak staining of capillaries No hepatic or reticulin staining |
| Abdominal wall, muscle and connective tissue | No staining |
| Skin (from sebaceous cyst) | Sebaceous gland with central staining |
| Myometrium, endometrium, erosa and ovary | No staining |
| Fallopian tubes | Mucin staining on surface epithelium |

Recognition of normal tissue was minimal and restricted to weak staining of the upper gastrointestinal tract basement membrane, mucin staining of stomach and fallopian tubes and weak staining of liver capillaries (Table 1).

A cell line expressing SC101/29 was deposited with ECACC under Accession no. 01050118.

EXAMPLE 2

Exposure of Tumour Cells to SC101 Antibodies

Methods and Results
Experiment 1
5×10$^4$ C170 (colorectal tumour) cells were incubated with various dilutions of antibody and left for 1 hour on ice. Following extensive washing the cells were mixed with a FITC labelled anti-mouse conjugate for a further 30 minutes. After washing for a second time the cells were fixed in proprietary cellfix and bound fluorescence measured by flow cytometry. The profiles show the analyses of the forward (FSCH) and side (SSH) scatter measurements made on the treated cells revealing the alteration in cell size and granularity following antibody treatment. During the routine characterisation of this family of antibodies it was noted that disaggregated tumour cells or cultured cell-lines exposed to SC101 rapidly shrank and increased their granularity (see FIG. 7).

Experiment 2
1×10$^5$ C170, HT29 or HL60 tumour cells in suspension were incubated with various dilutions of SC101 antibody and appropriate controls for 1 hour at room temperature. The cells were then washed, resuspended in proprietary binding buffer and stained with FITC labelled Annexin V and Propidium Iodide. The cells were then analysed by dual colour flow cytometry to determine the number of cells staining positive under the various conditions used. Cells staining with Annexin alone are in the early stages of apoptosis whereas cells staining with both Annexin and propidium iodide are in late stage apoptosis or necrosis.

The results show that Annexin V binding is increased following treatment of C170 cells with SC101 antibody but also reveals that propidium iodide staining is increased. This dual staining suggests that the positive cells are entering late stage apoptosis. These studies with Annexin-V showed that following a 1 h exposure of cells to SC101, phosphatidylserine was exposed on the outer surface of the cell membrane indicating the onset of apoptosis (see FIG. 8).

Experiment 3
3×10$^4$ Colorectal C170 cells were aliquoted into individual wells of a flat-bottomed 96-well plate and left to adhere overnight. The following day the cells were treated with various dilutions of SC101 antibody or appropriated controls and left for a further 5 days. The cultures were then washed and stained with crystal violet to determine the number of viable cells left in each well. The results were recorded by optical density at 490 nm and plotted in comparison with suitable negative controls.

Figure 9A:
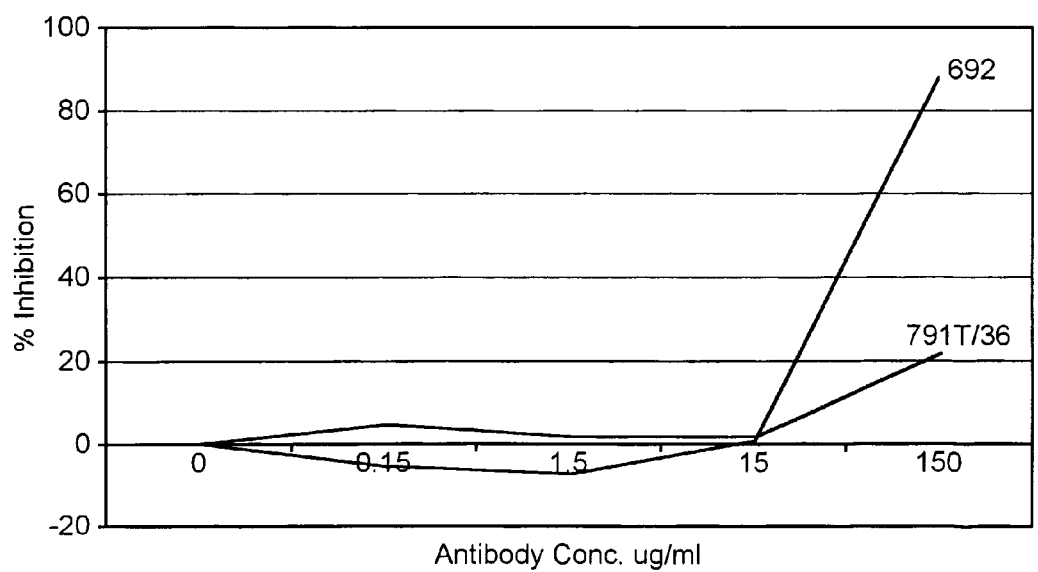
Figure 9B:
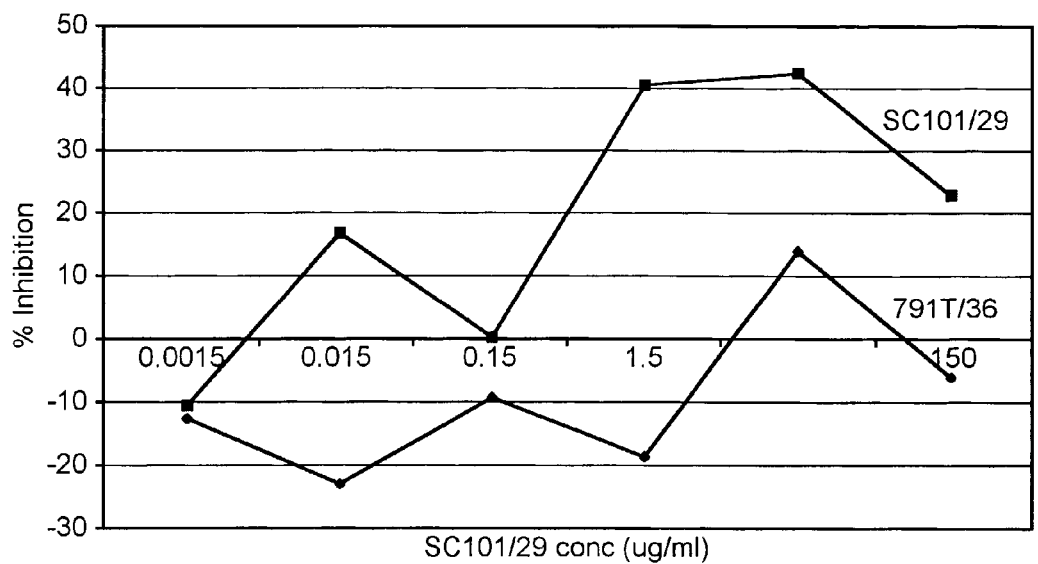

Significantly higher concentrations (compared to the concentrations used in those experiments described above) of antibody were required to inhibit the proliferation of adherent cell-lines growing as monolayer cultures (see FIG. 9a). These results suggest that deprivation of matrix attachment and cell-cell signaling increases the sensitivity of cells to treatment with SC101, enabling the antibody to induce increased Apoptosis and eventual cell death. Numerous studies have documented the importance of the cellular matrix in solid tumours as it stimulates survival signals through adhesion molecules such as the integrins. If this matrix support is removed these survival signals are absent and the sensitivity of the cells to potentially apoptotic stimuli is increased.

Experiment 4
In a further experiment, 3×10$^4$ leukaemic HL-60 cells were aliquoted into individual wells of a flat-bottomed 96-well plate. The cells were then treated with various dilutions of SC101 antibody or appropriate controls and left for 5 days. The cultures were then washed and stained with crystal violet to determine the number of viable cells in each well. The results were recorded by optical density at 490 nm and are plotted in comparison with suitable negative controls. The results show that at higher concentrations of SC101 HL-60 cell growth is significantly reduced compared with control cultures. These studies showed that high doses of SC101 could also inhibit the proliferation of HL60 cells in culture (see FIG. 9b).

Experiment 5
In a further experiment, 1×10$^5$ HL-60 myeloid leukaemic cells were incubated with SC101/29 monoclonal antibody appropriate controls at various dilutions, washed and stained with PE conjugated AP02.7 antibody. The cells were then analysed by flow cytometry to determine the number of positively stained cells in each case. The results shown in FIG. 10 show that SC101 antibody bound specific myeloid leukaemic cell lines and under certain conditions could induce apoptosis as measured by flow cytometry and Apo2.7, an antibody known to recognise a mitochondrial antigen exposed at the onset of Apoptosis.

EXAMPLE 3

Studies Using SC101/29 and Cisplatin

Methods and Results
Experiment 1
$3 \times 10^4$ Colorectal C170 cells were aliquote into individual wells of a flat-bottomed 96-well plate and left to adhere overnight. The following day the cells were treated with various dilutions of SC101 antibody or appropriate controls for 1 hour at room temperature. The cultures were then washed once and incubated in goat anti-mouse antibody at 100 ug/ml for 30 minutes at room temperature. The cultures were then re-washed and left overnight in culture medium with or without cisplatin. The following day the cultures were washed, lysed and tested for the presence of fragmented DNA by a Cyto Death ELISA (Roche). The results were recorded by optical Density measurements at 405 nm. FIG. 11 shows that cisplatin at 3 μg/ml induces apoptosis but that SC101 alone at concentrations up to 30 pg/ml fails to induce significant apoptosis. However when SC101 is added to cisplatin, increased apoptosis is observed. These results demonstrate that increased Apoptosis is observed when SC101 and Cisplatin are administered together and that the increase in Apoptosis is greater than the added effect of administering SC101 and Cisplatin separately.

The plots shown in FIG. 11 demonstrate the synergistic effect of SC101 antibody on Cisplatin treated cells with significantly increased levels of fragmented DNA indicative of increased apoptosis.
Experiment 2
Colorectal tumour cells were exposed to cisplatin (0-0.05 μg/ml) for 4 hrs at 37° C. and then SC101/29 (0-50 μg/ml) antibody was added. The cells were left for 4 days when the number of viable cells was determined by crystal violet staining and optical density reading at 550 nm. FIG. 12 shows that cisplatin at 1 μg/ml and SC101/29 both induce 10% inhibition of C170 cell growth. The combination of drug and antibody are synergistic, inducing a 50% reduction in cell growth.

EXAMPLE 4

Studies Using SC101/29 and 5 Fluorouracil

Methods and Results
$3 \times 10^3$ C170 cells were plated into microtitre plates and left overnight to adhere. 5 FU was added to a final concentrations of 0.25 and 0.5 μg/ml. SC101/29 antibody was also added at concentration of 1-50 μg/ml. Cells were left for 5 days at 37° C. prior to staining with crystal violet and reading the optical density reading at 550 nm to assess the number of cells. As shown in FIG. 13, a 10% in C170 cell growth is observed at a dose of 20 μg/ml of SC101/29. However, in combination with a non-toxic dose of 5 Fluorouracil (0.25 μg/ml) there was a 70% reduction in cell growth.

These studies, in combination with the studies described in Example 3 demonstrate that SC101 increases the sensitivity of cultured C170 cells to the effects of Cisplatin and 5-Fluorouracil and that SC101, Cisplatin and 5-Fluorouracil act synergistically in reducing cell growth (inducing apoptosis).

EXAMPLE 5

Studies Using SC101/29 and Tamoxifen, Doxorubicin, Irinotecan, Mitomycin C, Oxaliplatin and Raltitrexed Methods and Results Experiment 1-C170 Colorectal Cells.
$1 \times 10^3$ Colorectal C170 cells were aliquote into individual wells of a flat bottomed 96-well plate and left to adhere overnight at 37° C. The following day the cells were treated with Tamoxifen at final concentrations of 10, 3, 1, 0.3, 0.1 and 0 μM. Against each concentration of Tamoxifen the following concentrations of SC101/29 were titrated: 10, 3, 1, 0.3 and 0 μg/ml. As a negative control 791T/36 at concentrations 100, 30, 10, 3 and 0 μg/ml, was titrated against each concentration of Tamoxifen used. Duplicate wells were used. Cells were left for 5 days at 37° C. prior to the addition of MTS reagent to each well and optical density reading at 490 nm. FIGS. 14*a-e* show the effect of SC101/29 alone (a), 791T/36 alone (b), Tamoxifen alone (c), SC101/29 in combination with Tamoxifen (d), and 791T/36 in combination with Tamoxifen (e) on C170 growth at the concentrations stated. The minimum concentrations of SC101/29 and Tamoxifen giving the maximum degree of synergy were selected and plotted (FIG. 15). FIG. 15 also represents parallel experiments measuring the synergistic/additive effect of SC101/29 in combination with 5-FU, Cisplatin, Doxorubicin, Irinotecan, Mitomycin C, Oxaliplatin and Raltitrexed on C170 growth.
Experiment 2—MDA-MB468 Breast Cancer Cells.
Using the same method, the effect of SC101/29 alone and in combination with Tamoxifen and Doxorubicin on the growth of the Breast carcinoma cell line MDA-MB-468 was investigated. The effect of SC101/29 alone and in combination with Tamoxifen is shown in FIGS. 16*a-e* Synergy between SC101 and Tamoxifen or Doxorubicin is demonstrated by the graph shown in FIG. 17. The concentrations of SC101/29 in combination with Tamoxifen and Doxorubicin which yield the largest degree of synergy is also shown by FIG. 17.

EXAMPLE 6

Xenograft Experiments

Method and Results
Mice were explanted with 3 mm3 pieces of C170 xenografts. Groups of mice were treated with 5 FU/leucovorin (12.5 mg/Kg) by intravenous infusion on days 1, 3, 5, 7, 21 and 22. On the same days mice were also injected intra peritoneally with 0.2 mg of SC101/29 monoclonal antibody. Control mice received either SC101/29 alone or control mouse IgG antibody with 5 FU/leucovorin. Tumour size was measured by callipers and tumour cross sectional area calculated on days 12, 16, 19 and 23. At the termination of the experiment tumours were weighed to assess anti-tumour efficacy. Animals were weighed to assess the toxicity of treatment.

SC101 antibody significantly inhibited tumour growth at a dose of 0.2 mg. 12.5 mg/Kg of 5 FU/leucovorin also inhibited tumour growth (FIG. 18 and FIG. 20). However, the combination was even more effective (FIGS. 18 and 20). However, none of the treatments were toxic to the animals as they showed normal weight gain (FIG. 19). These results suggest that the anti-tumour efficacy of chemotherapy may be enhanced by treatment with SC101 monoclonal antibodies.

The invention claimed is:

1. A method of treatment of a tumor in a patient, wherein the tumor expresses both Lewis$^y$ and Lewis$^b$ antigens, comprising:
   administering to the patient an effective amount of a naked antibody or fragment thereof, in combination with an active agent, wherein the antibody or fragment thereof binds to both Lewis$^y$ and Lewis$^b$ haptens and does not bind to H blood group antigen wherein the antibody comprises all the complementarity determining regions (CDRs) of the antibody produced by the cell line deposited as ECACC Accession No. 01050118.

2. The method as claimed in claim 1, wherein the antibody comprises a constant region of human antibody class IgM, IgA, IgG$_2$ or IgG$_3$.

3. The method as claimed in claim 1, wherein the active agent is a chemotherapeutic agent.

4. The method as claimed in claim 3, wherein the chemotherapeutic agent is selected from the group consisting of doxorubicin, taxol, 5-fluorouracil (5 FU), leucovorin, irinotecan, mitomycin C, oxaliplatin, raltitrexed, tamoxifen and cisplatin.

5. The method as claimed in claim 1, wherein the active agent is selected from the group consisting of aspirin, paracetamol, ibuprofen, ketoprofen, morphine and anti-emetics.

6. The method as claimed in claim 1, wherein the antibody and active agent are administered simultaneously.

7. The method as claimed in claim 1, wherein the antibody and active agent are administered sequentially.

8. The method of claim 1, wherein the tumor is selected from the group consisting of colorectal, breast, ovarian, gastric, leukemia, lung, liver, skin, and myeloid cancer.

9. The method of claim 1, wherein the patient is a mammal.

10. The method of claim 9, wherein the patient is a human.

11. A method of treating a tumor in a human patient, wherein the tumor expresses both Lewis$^y$ and Lewis$^b$ antigens, comprising:
    administering to the human patient an effective amount of an isolated antibody or fragment thereof comprising all the complementarity determining regions (CDRs) of the antibody produced by the cell line deposited as ECACC Accession No. 01050118, which antibody or fragment thereof specifically binds to both Lewis$^y$ and Lewis$^b$ haptens and does not bind to H blood group hapten.

12. The method of claim 11, wherein the isolated antibody is produced by the cell line deposited as ECACC Accession No. 01050118.

13. A method of treating a tumor in a human patient, wherein the tumor expresses both Lewis$^y$ and Lewis$^b$ antigens, comprising:
    administering to the human patient an effective amount of an isolated antibody fragment comprising all the complementarity determining regions (CDRs) produced by a cell line deposited as ECACC Accession No. 01050118, characterized by specifically binding to Lewis$^y$ and Lewis$^b$ and not binding to Lewis$^x$.

14. The method of claim 13, wherein the isolated antibody fragment further characterized by not binding to H blood group antigen by thin layer chromatography.

15. A method of treating a tumor in a human patient, wherein the tumor expresses both Lewis$^y$ and Lewis$^b$ antigens, comprising:
    administering to the human patient an effective amount of an isolated antibody fragment comprising all the complementarity determining regions (CDRs) produced by a cell line deposited as ECACC Accession No. 01050118, characterized by specifically binding to Lewis$^y$ and Lewis$^b$ and not binding to H blood group antigen by thin layer chromatography.

* * * * *